US009132162B2

(12) United States Patent
Fisher et al.

(10) Patent No.: US 9,132,162 B2
(45) Date of Patent: *Sep. 15, 2015

(54) MUSCADINE COMPOSITIONS WITH ANTI-OXIDANT ACTIVITY

(71) Applicant: Shaklee Corporation, Pleasanton, CA (US)

(72) Inventors: Laurel A. Fisher, San Francisco, CA (US); Teodoro T. Ianiro, Concord, CA (US); William J. Mergens, West Palm Beach, FL (US); Nasrin Zamanian, Saratoga, CA (US)

(73) Assignee: Shaklee Corporation, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/784,566

(22) Filed: Mar. 4, 2013

(65) Prior Publication Data

US 2013/0184228 A1     Jul. 18, 2013

Related U.S. Application Data

(63) Continuation-in-part of application No. 13/056,536, filed as application No. PCT/US2009/052343 on Jul. 31, 2009, now Pat. No. 8,568,804, and a continuation-in-part of application No. 13/056,559, filed as application No. PCT/US2009/052346 on Jul. 31, 2009, now Pat. No. 8,512,771.

(60) Provisional application No. 61/085,369, filed on Jul. 31, 2008, provisional application No. 61/085,371, filed on Jul. 31, 2008.

(51) Int. Cl.
| A61K 36/87 | (2006.01) |
| A61K 31/05 | (2006.01) |
| A61K 31/7048 | (2006.01) |
| A61K 31/37 | (2006.01) |

(52) U.S. Cl.
CPC .............. *A61K 36/87* (2013.01); *A61K 31/05* (2013.01); *A61K 31/37* (2013.01); *A61K 31/7048* (2013.01)

(58) Field of Classification Search
None
See application file for complete search history.

(56) References Cited

U.S. PATENT DOCUMENTS

| 6,190,716 B1 | 2/2001 | Galbreath, Jr. |
| 6,638,545 B1 | 10/2003 | Rombi |
| 8,017,147 B2 | 9/2011 | Mazed et al. |
| 8,075,929 B2 | 12/2011 | Shrikhande et al. |
| 8,114,445 B2 | 2/2012 | Hastings |
| 8,173,181 B2 | 5/2012 | Ferguson et al. |
| 8,182,849 B2 | 5/2012 | Endo et al. |
| 8,512,771 B2 * | 8/2013 | Ianiro et al. .................... 424/766 |
| 8,568,804 B2 * | 10/2013 | Fisher et al. .................... 424/766 |
| 2004/0234671 A1 | 11/2004 | Ector et al. |
| 2005/0158376 A1 | 7/2005 | Sardi et al. |
| 2006/0024392 A1 | 2/2006 | Magnuson et al. |
| 2006/0121137 A1 | 6/2006 | Hartle et al. |
| 2006/0277887 A1 | 12/2006 | Dalton et al. |
| 2007/0003644 A1 | 1/2007 | Randhava et al. |
| 2009/0176718 A1 | 7/2009 | Ribnicky et al. |
| 2010/0004344 A1 | 1/2010 | Dallas |
| 2011/0177182 A1 | 7/2011 | Ianiro et al. |
| 2011/0177183 A1 | 7/2011 | Ianiro et al. |

FOREIGN PATENT DOCUMENTS

| CN | 1343100 A | 4/2002 |
| CN | 1698733 A | 11/2005 |
| CN | 1956733 A | 5/2007 |
| JP | 2002293736 A | 10/2002 |
| WO | WO 98/17250 A1 | 5/1997 |
| WO | WO 2005/099761 A1 | 10/2005 |
| WO | WO 2005-110404 A2 | 11/2005 |
| WO | WO 2007/074472 A2 | 7/2007 |
| WO | WO 2008/144019 | 11/2008 |

OTHER PUBLICATIONS

Ector et al., "Resveratrol Concentration in Muscadine Berries, Juice, Pomace, Purees, Seeds and Wines," *Am. J. Enol. Vitic.*, vol. 47(1):57-62 (1996).
Soleas et al., "Comparative Evaluation of Four Methods for Assay of cis- and trans- Resveratrol," *Am. J. Enol. Vitic.*, vol. 48(2):169-176 (1997).
Percival and Sims, "Wine Modifies the Effects of Alcohol on Immune Cells of Mice $^{1-3}$," *J. of Nutrition*, vol. 130(5):1091-1094 (2000).
Chen et al., "High-speed counter-current chromatography separation and purification of resveratrol and piceid from *Polygonum cuspidatum*," *J. of Chromatography A*, vol. 907:343-346 (2001).
Pastrana-Bonilla et al., "Phenolic Content and Antioxidant Capacity of Muscadine Grapes," *J. Agricultural and Food Chemistry*, vol. 51:5497-5503 (2003).
Ke-lin "Impact of Grape Seed Extract on Human Health," *China Drinks*, pp. 46-47 (2003).
Yilmaz and Toledo, "Major Flavonoids in Grape Seeds and Skins: Antioxidant Capacity of Catechin, Epicatechin, and Gallic Acid," *J. Agric. Food. Chem.*, vol. 52:255-260 (2004).
Dansby "Evaluation of the Antioxidant and Biological Properties of Muscadine Grape Seed Extracts," *Dissertation North Carolina State University*, pp. ii-v, 1, 45 (2006).
Xiao-jia et al. "Review on Health Function, Processing Technology and Determination of Resveratrol," *Food Research and Development*, vol. 27(2):123-126 (2006).

(Continued)

*Primary Examiner* — Susan Hoffman
(74) *Attorney, Agent, or Firm* — Klarquist Sparkman, LLP

(57) ABSTRACT

Antioxidant compositions are disclosed that include muscadine pomace extract and resveratrol from a source other than muscadine. In other examples the composition also includes polyphenols from a source other than muscadine. The compositions increase the expression of antioxidant genes and/or genes associated with mitochondrial biogenesis.

21 Claims, No Drawings

(56) References Cited

OTHER PUBLICATIONS

Perron and Brumaghim "A Review of the Antioxidant Mechanisms of Polyphenol Compounds Related to Iron Binding," *Cell Biochem Biophys*, 53:75-100 (2009).

Cardona et al. "Color and Polyphenolic Stability in Extracts Produced from Muscadine Grape (*Vitis rotundifolia*) Pomace," *J. of Agriculture and Food Chemistry*, vol. 57:8421-8425 (2009).

Sandhu and Gu "Antioxidant Capacity, Phenolic Content, and Profiling of Phenolic Compounds in the Seeds, Skin, and Pulp of *Vitis rotundifolia* (Muscadine Grapes) as Determined by HPLC-DAD-ESI-MS", *J. of Agriculture and Food Chemistry*, vol. 58:4681-4692 (2010).

Ghanim et al. "A Resveratrol and Polyphenol Preparation Suppresses Oxidative and Inflammatory Stress Response to a High-Fat, High-Carbohydrate Meal," *J. Clin. Endocrinol Metab.*, vol. 96(5):1409-1414 (2011).

Mertens-Talcott et al. Low Concentrations of Quercetin and Ellagic Acid Synergistically Influence Proliferation, Cytotoxicity and Apoptosis in MOLT-4 Human Leukemia Cells [1-3], *J. Nutrition* 133:2669-2674 (2003).

Kurilich et al. "Plasma and Urine Responses Are Lower for Acylated vs. Nonacylated Anthocyanins from Raw and Cooked Purple Carrots," *J. Agric. Food Chem.* 53(16):6537-6542 (2005).

Mertens-Talcott et al. "Ellagic acid and quercetin interact synergistically with resveratrol in the induction of apoptosis and cause transient cell cycle arrest in human leukemia cells," *Cancer Letters* 218:141-151 (2005).

Hudson et al. "Inhibition of Prostate Cancer Growth by Muscadine Grape Skin Extract and Resveratrol through Distinct Mechanisms," *Cancer Research* 67(17):8396-8405 (2007).

Sapcanin et al. "Antioxidant Capacity in the Lipophilic Fraction of Alzheimer's Brain Tissues," *Bosnian J. Basic Medical Sciences* 7(4):317-321 (2007).

God et al. "Anticancer Effects of Four Varieties of Muscadine Grapes," *J. of Medical Food* 10(1):54-59 (2007).

J. Ponce "Chemical and Economic Analysis of Value-added Product from Muscadine Grape Pomace," *University of Florida* http://ufdc.ufl.edu/UFE0021495/00001 (2007) *Not catalogued until Apr. 2, 2010.

T. Vashisth "Evaluation of Drying Technologies for Muscadine Pomace to Produce an Antioxidant Rich Functional Food Ingredient," *The University of Georgia* http://hdl.handle.net/10724/11195 (2009).

Soto et al. "Recovery and Concentration of Antioxidants from Winery Wastes," *Molecules* 17:3008-3024 (2012).

* cited by examiner

MUSCADINE COMPOSITIONS WITH ANTI-OXIDANT ACTIVITY

RELATED APPLICATIONS

This application is a continuation-in-part of U.S. application Ser. No. 13/056,536, filed Jan. 28, 2011, now U.S. Pat. No. 8,568,804, which is the §371 U.S. National Stage of International Application No. PCT/US2009/052343, filed on Jul. 31, 2009, which was published in English under PCT Article 21 (2), which in turn claims the benefit of and priority to U.S. Provisional Application No. 61/085,369 filed on Jul. 31, 2008, all of which applications are incorporated herein in their entirety.

This application is also a continuation-in-part of U.S. application Ser. No. 13/056,559, filed Jan. 28, 2011, now U.S. Pat. No. 8,512,771, which is the §371 U.S. National Stage of International Application No. PCT/US2009/052346, filed on Jul. 31, 2009, which was published in English under PCT Article 21 (2), which in turn claims the benefit of and priority to U.S. Provisional Application No. 61/085,371 filed on Jul. 31, 2008, all of which applications are incorporated herein in their entirety.

FIELD

This invention relates to an antioxidant composition that contains a muscadine grape extract.

BACKGROUND

Reactive oxygen species (ROS) are obligatory byproducts of aerobic metabolism and thus are generated continuously in humans and other organisms. Humans are also exposed to ROS from exogenous/environmental sources such as pollution, sunlight and diet. While there are different chemical forms of ROS, they all produce deleterious actions on the structure and function of cellular constituents and macromolecules. The intensity of ROS generation/exposure is termed oxidative stress.

Oxidative stress is considered to be associated with the pathogenesis of chronic inflammatory diseases such as diabetes, cancer, atherosclerosis and other cardiovascular diseases, as well as with degenerative neurological diseases such as Alzheimer's disease and Parkinson's disease. Moreover, multiple lines of evidence support the view that oxidative stress is a central mechanism underlying normal aging. Accordingly, a need exists to develop compositions and methods to inhibit oxidative stress.

The moderate use of wine has been reported to lower the incidence of cardiovascular diseases and their consequent mortality in wine-drinking populations. Moderate wine intake has also been reported to provide a neuroprotective effect against dementia. Grapes contain several bioactive polyphenolic compounds, including flavonoids (such as flavan-3-ols and oligomers thereof known as proanthocyanidins; flavonols, anthocyanins, and flavanones) and non-flavonoids (such as phenolic acids, tannins and stilbene derivatives, for example resveratrol). The non-flavonoid resveratrol has been considered to mediate many of the beneficial effects of grape products on the human cardiovascular system. The protective and anti-inflammatory effects of the flavonoids are believed to be due to free radical scavenging, various effects on cellular signaling pathways and gene expression, and selective interference with a multitude of factors that affect the cell division cycle of rapidly and abnormally proliferating mammalian cells.

SUMMARY

An antioxidant composition is disclosed that includes a muscadine (*Vitis rotundifolia*) pomace extract, and resveratrol from a source other than muscadine, wherein a ratio of muscadine pomace extract polyphenols to trans-resveratrol is in the range of 0.1/1 to 10/1 (weight to weight) and the composition has a polyphenol content of at least 2%, for example at least 4%, 5% or 10-35%, such as 12-32%. In some examples the ratio of polyphenols to trans-resveratrol is at least 0.75 to 1. In other examples, the resveratrol from a source other than muscadine is from Japanese knotweed, melinjo (*Gnetum gnemon*), red wine, peanut shells or grapevines. In some embodiments the muscadine pomace extract is a concentrated muscadine pomace extract, for example concentrated to a solids content of at least 40%.

In other examples, the composition also includes polyphenols, such as anthocyanins, from a source other than muscadine, for example from one or more of elderberry, black currant, blueberry, black raspberry, red raspberry, blackberry, bilberry, cloudberry, chokeberry, gooseberry, grape or purple carrot, or an extract of any of them. In particular embodiments the polyphenols, such as anthocyanins, are in an extract of elderberry fruit. In other examples, the polyphenols from sources other than muscadine are present in a ratio of 1:3 to 2:1 with polyphenols from the muscadine pomace extract.

The composition can be combined with carriers and/or food flavorings and colorings, and/or included in an ingestible composition such as a food product or nutritional supplement.

In particular examples, the muscadine pomace extract is a solvent extract, such as a water extract, of muscadine pomace. The muscadine pomace extract may be either a bronze muscadine pomace extract, a purple muscadine pomace extract, or a mixture of bronze and purple muscadine pomace extract, for example a mixture in a ratio of bronze muscadine pomace extract to purple muscadine pomace extract ranging from 0.1 to 10 (weight to weight). The solubility of ellagic acid is improved by mixing the bronze and purple pomace extracts.

A method of inhibiting oxidation in a subject is also disclosed herein. In some examples the method includes administering an antioxidative effective amount of the composition. In some embodiments the method increases $ORAC_{lipophilic}$ in a subject to whom the composition is administered. In other embodiments, the effective amount of the composition increases one or more of mitochondrial oxygen consumption, lipophilic ORAC, mitochondrial biogenesis, or expression of mitochondrial biogenesis or antioxidant genes. Examples of the mitochondrial biogenesis genes are one or more of NRF1, SIRT3, COX, and examples of the antioxidant genes include one or more of NRF2, NQO-1, and GST-P1. In certain embodiments of the method a subject is selected who is in need of increased mitochondrial biogenesis and/or antioxidant activity, or the subject is in need of an increase in antioxidant activity in lipophilic tissue. The composition is administered to the subject to increase one of more of these activities.

Another disclosed embodiment is a method of making an antioxidant composition by combining a muscadine (*Vitis rotundifolia*) pomace extract with resveratrol from a source other than muscadine in a ratio of muscadine pomace extract polyphenols to trans-resveratrol in the range of 0.1/1 to 10/1 (weight to weight), and the resulting composition has a polyphenol content of at least 2%, for example at least 4%.

The muscadine pomace extract may optionally be concentrated prior to combining it with the resveratrol from a source other than muscadine. In some examples the muscadine pomace extract and resveratrol are combined with polyphenols (such as anthocyanins) from a source other than muscadine, such as from one or more of an extract of elderberry, black currant, blueberry, black raspberry, red raspberry, blackberry, bilberry, cloudberry, chokeberry, gooseberry, grape or purple carrot.

In particular embodiments, the method includes combining a mixture of bronze and purple muscadine pomace extract and elderberry fruit extract having a polyphenol content of at least 5% with a Japanese Knotweed root extract. In certain examples the Japanese Knotweed root extract is at least 98% resveratrol, and/or the muscadine pomace extract is a mixture of bronze and purple muscadine pomace extract. In some embodiments of the method the bronze and purple muscadine pomace extracts are combined or otherwise present in a ratio that ranges from 0.1 to 10.

In another embodiment of the method of making an antioxidant composition, bronze and purple muscadine pomace are solvent extracted, either separately or together, to obtain a mixture of bronze and purple muscadine pomace extract containing solubilized ellagic acid, then the mixture of bronze and purple muscadine pomace extract is concentrated, for example to a solids content of at least 40%. The concentrated bronze and purple muscadine pomace extract mixture is combined with resveratrol from a source other than the muscadine pomace extract to obtain an antioxidant mixture, such that the ratio of muscadine pomace extract polyphenols to trans-resveratrol in the antioxidant mixture is in a range of 0.1/1 to 10/1 (weight to weight), and the resulting antioxidant composition has a polyphenol content of at least 2%.

In other embodiments of the method, the antioxidant composition is further combined with polyphenols (such as anthocyanins) from a source other than muscadine, for example by adding elderberry fruit extract to the antioxidant composition. In particular embodiments the components are combined so that the antioxidant composition includes at least 10% polyphenols, for example up to 35% polyphenols, such as 12-32%.

The method may further include incorporating the antioxidant composition into an ingestible product that provides the composition in an ingestible form. For example, the composition is combined with one or more carrier, food flavoring and/or coloring, or is incorporated into a food supplement, nutraceutical, or other unit dosage form.

The foregoing and other objects, features, and advantages of the invention will become more apparent from the following detailed description.

DETAILED DESCRIPTION

I. Abbreviations and Terms (a) Abbreviations

COX: cytochrome c oxidase subunit VIIc1
FRAP: Ferric Reducing Ability of Plasma
GST-P1: glutathione S transferase pi1
mg: milligram
ml: milliliter
NQO-1: NAD(P)H quinone oxido/reductase 1
NRF1: nuclear respiratory factor 1
NRF2: nuclear factor (erythroid-derived 2)-related factor 2
PGC1-α: peroxisome proliferator-activated receptor gamma coactivator-1α
ORAC: Oxygen Radical Absorbance Capacity
ROS: Reactive oxygen species
SIRT1: sirtuin 1
SIRT3: sirtuin 3
TE: Trolox Equivalent
TEAC: Trolox Equivalent Antioxidant Capacity
TLR4: Toll-like receptor 4
wt: weight (b) Terms The following explanations of terms and methods are provided to better describe the present disclosure and to guide those of ordinary skill in the art in the practice of the present disclosure. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. It is further to be understood that any quantitative values are approximate whether the word "about" or "approximately" or the like are stated or not. All percentages and ratios are calculated by weight unless otherwise indicated.

Administration: To provide or give a subject an agent by any effective route. Exemplary routes of administration include, but are not limited to, oral, injection (such as subcutaneous, intramuscular, intradermal, intraperitoneal, intravenous, and intratumoral), sublingual, transdermal, intranasal, topical and inhalation routes.

Anthocyanin: A water-soluble vacuolar pigment found in many plants that may appear red, purple or blue depending on the pH. Anthocyanins belong to a parent class of molecules called flavonoids that are synthesized via a phenylpropanoid pathway. Anthocyanins have the general chemical structure shown below:

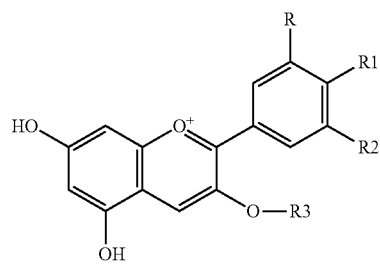

Chemical structure of anthocyanins

"Anthocyanins from a source other than muscadine" refers to anthocyanins obtained from a source other than a muscadine grape. Examples of such non-muscadine sources include elderberry, black currant fruit, blueberry, black raspberry, red raspberry, bilberry, grape or purple carrot.

Antioxidant activity: Activity that reduces oxidative stress, for example by scavenging and neutralizing oxidative free radicals. Antioxidant activity can be measured using the methods disclosed herein as well as those known in the art, including the Oxygen Radical Absorbance Capacity (ORAC) assay, the Ferric Reducing Ability of Plasma (FRAP) assay, and the Trolox Equivalent Antioxidant Capacity (TEAC) assay. For example, a composition has antioxidant activity and can be used as an antioxidant if it has a total ORAC of at least 24 μmole Trolox Equivalents per mg polyphenol (μmoleTE/mg polyphenol). Antioxidant activity can also be measured by an increase in the expression of genes such as NRF2, NQO-1 and GST-P1.

Antioxidant composition: A composition that has antioxidant activity.

Antioxidative effective amount: An amount sufficient to induce an antioxidant effect in a subject to whom the amount of a composition is administered. In particular examples, the amount is sufficient to induce mitochondrial biogenesis or antioxidant activity. In some examples the induction of this activity is indicated by an increase in the expression of genes associated with increasing mitochondrial biogenesis or antioxidant activity. In other examples, the composition induces a selectively synergistic increase in $ORAC_{lipophilic}$ antioxidant activity by increasing $ORAC_{lipophilic}$ to a greater extent than what would be predicted from the addition of the $ORAC_{lipophilic}$ values of the individual components of the composition. Induction of mitochondrial biogenesis is associated with anti-aging processes and may be associated with an increase in the expression of mitochondrial biogenesis genes such as NRF1, SIRT3 and COX.

Elderberry (*Sambucus nigra*): A plant belonging to the Adoxaceae family found in Europe and North America with several regional varieties or subspecies. The flowers are in flat corymbs. The berries are black to glaucous blue and contain anthocyanins and other polyphenolics (for example, proanthocyanidins and flavonols such as quercetin) in which the amount and type of anthocyanins and other polyphenolics vary depending upon the variety.

An "elderberry extract" is a material obtained by extracting an elderberry according to any extraction method known to one of skill in the art, so long as it has the desired activity (e.g., color stabilizing activity, antioxidant activity or a combination thereof). For example, the elderberry extract can include a fruit juice obtained by compressing elderberry fruit, or an extract obtained by extracting whole fruit of elderberry or a suitable portion of skin or seed of the fruit according to known extraction methods, such as solvent (for example water) extraction. Also, a crushed product of an elderberry fruit or a dried elderberry fruit concentrate can be used as "an elderberry extract."

Excipient: An inactive substance used as a carrier for the active ingredients of a composition. Excipients can include substances that are used as bulk in formulations with very potent active ingredients, allow for convenient and accurate dosage, stabilize the active ingredients, and make the delivery system optically and/or organoleptically acceptable. Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In a particular example, the disclosed anti-aging supplement includes the following excipients: glycerin, sorbitol, colloidal silicon dioxide, and a natural flavoring additive.

Extract: To separate a substance from a matrix. An extract is also the substance made by extracting a part of a raw material, for example by using pressure or a solvent such as ethanol and/or water. Extracts may be in liquid or powder form. Particular examples of extracts disclosed herein are in liquid form. A "solvent extract" refers to an extract obtained by exposing a target to a liquid solvent that solubilizes the desired substance contained in a product. A "water extract" is an extract obtained by water extraction of a product. Solvent extracts remove target substances from the product according to the solubility of the target substance in the solvent.

Inhibiting (including preventing) cellular aging: Inhibiting (for example preventing) one or more processes associated with cellular aging, such as inhibiting free radical formation or activity in a subject who ingests the composition. Preventing cellular aging refers to an intervention that ameliorates a sign or symptom of cellular aging. Preventing includes prophylaxis to delay the onset of one or more processes associated with cellular aging. Prevention or inhibition of cellular aging does not require a total absence of cellular aging. In a particular example, a disclosed composition decreases or delays a process associated with cellular aging by at least 10%, at least 20%, at least 50%, or even at least 90%. Such decreases can be measured using the methods disclosed herein as well as those known in the art.

Japanese Knotweed (*Fallopia japonica, Polygonum cuspidatum*): a large herbaceous perennial plant which is native to Eastern Asia in Japan, China and Korea. It is a concentrated source of resveratrol and its glucoside piceid (up to 0.05 to 0.2% of fresh weight).

Mitochondrial biogenesis: Production of new mitochondria in the cell. Mitochondrial biogenesis is activated by numerous different signals during times of cellular stress or in response to environmental stimuli. The mitochondrion is a key regulator of cellular metabolic activity and is also an important organelle in both production and degradation of free radicals. Higher mitochodrial copy number (or higher mitochondrial mass) is considered cytoprotective. Lower mitochondrial density is associated with advancing physiological age. Mitochondria are produced from the transcription and translation of genes both in the nuclear genome and in the mitochondrial genome. Important regulators of mitochondrial biogenesis appear to be the sirtuin 3 (SIRT3) and the peroxisome proliferator-activated receptor gamma (PGC) family of transcriptional coactivators, including PGC-1α, PGC-1β, and the PGC-related coactivator, PRC. For example, PGC-1α is known to co-activate nuclear respiratory factor 2 (NRF2/GABPA), and together with NRF-2 coactivates nuclear respiratory factor 1 (NRF1). The NRFs, in turn, activate the mitochondrial transcription factor A (tfam), which is directly responsible for transcribing nuclear-encoded mitochondrial proteins.

Muscadine Grape (*Vitus rotundifolia*): Grapes native to the southeastern United States, and found in the wild from Delaware to the Gulf of Mexico and westward to Missouri, Kansas, Oklahoma, and Texas. Muscadines are well adapted to the warm, humid conditions of the southeastern United States. The fruit is borne in small, loose clusters of 3-40 grapes, quite unlike the large, tight bunches characteristic of European and American grapes. The round, 1 to 1½ inch fruits have a thick, tough skin and contain up to 5 hard, oblong seeds. In color the fruits range from greenish bronze through bronze, pinkish red, purple and almost black.

Many different varieties of muscadine grapes are available, including female (pistillate) varieties such as Black Beauty, Black Fry, Darlene, Fry, Higgins, Jumbo, Scuppernong, Sugargate, Summit, Supreme, and Sweet Jenny, and self-fertile varieties such as Carlos, Cowart, Dixieland, Dixie Red, Fry Seedless, Magnolia, Nesbitt, Noble, Redgate, Regale and Sterling.

For example the bronze colored varieties of muscadine grapes are identified by those skilled in the art as including Carlos, Chowan, Doreen, Higgins, Magnolia, Nevermiss, Pamlico, Roanoke, Scuppernong, Sterling, and Summit cultivars. Purple varieties are darker skinned then the bronze colored varieties and include Albermarle, Bountiful, Cowart, GA-1, Hunt, NC-1, Noble, Regale, Tarheel, and Jumbo. Some of the purple varieties are also referred to as Black colored.

The phytochemical constituents of the whole muscadine grape differ from *Vitis vinifera*. Muscadines have a higher total phenolic content distinguished by high ellagic, gallic, and flavonoid glycoside concentrations. The presence of ellagic acid in muscadine grapes is unique and is found in the form of free ellagic acid, ellagic acid glycosides, methoxylated derivatives and ellagitannins. Another unique feature is the anthocyanin chemistries observed in muscadines. Present as 3,5-diglucosides (as opposed to 3-glucosides) of delphinidin, cyanidin, petunidin, peonidin, and malvidin in non-acylated forms, these compounds and the natural color influence from other anthocyanins present within the grape impart a dark purple color to juice and pomace obtained from the purple varieties. Purple pomace extracts contain anthocyanins while bronze pomace extracts do not.

The red and purple colored anthocyanins found in purple muscadine grapes are polyphenolic compounds that have antioxidant properties. Purple and bronze muscadine grapes contain several other flavonoid classes of polyphenols with flavan-3-ols and their oligomers being the most abundant class and flavonols being the second most abundant flavonoids present in whole muscadines. The major phenolics reported for the muscadine skin fraction (in descending order) are ellagic acid, myricetin, quercetin, and kaempferol while those reported for seeds are epicatechin, catechin and gallic acid (Pastrana-Bonilla et al. *J. Agric. Food Chem.* 51:5497-5503, 2003).

Pharmaceutically Acceptable Vehicles: The pharmaceutically acceptable vehicles (carriers) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more compositions, such as one or more muscadine compositions, and additional pharmaceutical agents.

In general, the nature of the vehicle will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid vehicles can include, for example, pharmaceutical grades of mannitol, lactose, starch, or magnesium stearate. In addition to biologically-neutral vehicles, pharmaceutical compositions can contain minor amounts of non-toxic auxiliary substances, such as wetting or emulsifying agents, preservatives, and pH buffering agents and the like, for example sodium acetate or sorbitan monolaurate.

Polyphenols (also known as polyhydroxyphenols, phenolics and polyphenolics): A class of organic compounds characterized by the presence of multiple phenol structural units. Many of them are derived from plants, and can generally be divided into flavonoids, phenolic acids and stilbenes although there are multiple subclasses of flavonoids and phenolic acids. Polyphenols found in plants are usually complex mixtures of different polyphenol classes and moreover may be conjugated to sugar groups (polyphenol glycosides) or may occur in the aglycone form (without sugar group attachments). "Polyphenols from a source other than muscadine" refers to polyphenols that are present in or obtained from a product other than a muscadine grape and includes multiple classes of polyphenols such as flavonoids, tannins and phenolic acids. Examples of such non-muscadine sources include elderberry, black currant, blueberry, black raspberry, red raspberry, blackberry, bilberry, cloudberry, chokeberry, gooseberry, pomegranate, grape or purple carrot.

Pomace: The skins, seeds, and pulp remaining following juice extraction. In one example a pomace extract is a bronze muscadine pomace extract, a purple muscadine pomace extract or a combination thereof. Many different varieties of muscadine grape pomaces are available as starting materials, and they include female (pistillate) varieties such as Black Beauty, Black Fry, Darlene, Fry, Higgins, Jumbo, Scuppernong, Sugargate, Summit, Supreme, and Sweet Jenny, and self-fertile varieties such as Carlos, Cowart, Dixieland, Dixie Red, Fry Seedless, Magnolia, Nesbitt, Noble, Redgate, Regale and Sterling.

Muscadine pomace contains phenolic compounds, including gallic acid and ellagic acid, having antioxidant properties.

Purified: The term purified does not require absolute purity; rather, it is intended as a relative term. Thus, for example, a purified substance is one in which the substance is more enriched than the substance in its natural environment, for example in a fruit (e.g., grape). In one embodiment, a preparation is purified such that the substance represents at least about 5% (such as, but not limited to, at least 10%, 20%, 30%, 40%, 50%, 70%, 80%, 90%, 95%, 98% or 99%) of the total content of the preparation. In an example, a disclosed composition with antioxidant activity includes trans-resveratrol with a minimum purity of at least 50%, 70%, 80%, 90%, 95%, 98% or 99% of the total resveratrol preparation (by weight).

Purple carrot (*Daucus carota*): a cultivar of carrot containing anthocyanin pigments. A "purple carrot extract" can be obtained by extracting a purple carrot according to any extraction method known in the art, such as pressing or solvent extractions, so long as the extract has the desired activity (e.g., color stabilizing activity, antioxidant activity or a combination thereof). In an example, a purple carrot extract has the property of stabilizing muscadine color pigment and can therefore be subsequently utilized as color-stabilizing additive.

Resveratrol: A phytoalexin that is a stilbenoid, a derivate of stilbene, and is produced in plants with the help of the enzyme stilbene synthase. Resveratrol exists as two structural isomers: cis- and trans-resveratrol. Trans-resveratrol can undergo isomerisation to the cis-form when heated or exposed to ultraviolet irradiation.

Resveratrol is found in widely varying trace amounts, on average it is less than 0.0001% (of fresh weight) when measured in grapes, raspberries, mulberries, plums, peanuts, berries of *Vaccinium* species, including blueberries, bilberries, and cranberries, and some pines, such as Scots pine and eastern white pine; the richest natural sources of resveratrol aglycone (up to 0.05% of fresh weight) are the roots and stalks of giant knotweed and Japanese knotweed. In grapes, any resveratrol present is found primarily in the skin and seeds. The amount of resveratrol found in grape skins varies with the grape cultivar, its geographic origin, and exposure to fungal infection. However, as noted above, it is typically present in only trace amounts.

As used herein, the term resveratrol can include natural trans-resveratrol extracted from a plant, such as grapes, or synthetic trans-resveratrol. As used herein, the term resveratrol can include modified formulations of trans-resveratrol such as microencapsulated or water dispersible forms.

"Resveratrol from a source other than muscadine" refers to resveratrol that is present in or obtained from a product other than a muscadine grape (or any subcomponent of the muscadine grape, such as its seeds). Resveratrol is substantially absent from solvent-extracted (such as water-extracted) muscadine pomace, and in some disclosed examples the muscadine pomace solvent extract is substantially free from resveratrol until the resveratrol from another source is added to the extract.

Subject: Living multi-cellular vertebrate organisms, a category that includes both human and veterinary subjects, such as a companion animal, including a cat, dog or horse. A "subject in need of an increase in mitochondrial biogenesis and/or antioxidant activity" is a subject who may benefit from such an increase, such as a subject who desires to decrease signs of age, offset tissue damage caused by oxidation, and/or improve cardiovascular, neurological, tumor-related, skin-appearance or other conditions that are associated with oxidative stress.

Therapeutically Effective Amount: An amount of a composition that alone, or together with an additional agent(s) (for example additional antioxidants), induces the desired response (e.g., prevents or inhibits cellular aging). The preparations disclosed herein can be administered in therapeutically effective amounts.

II. Description of Several Embodiments

Plant agents have been studied extensively as a potential source of nutriceutical agents that can be used to reduce oxidative stress. Red grapes are among the many foods that have been the subject of intense research. The antioxidant effects of red grapes have been widely attributed to the polyphenolic compounds, such as resveratrol and procyanidins, the latter which appear in substantial quantities in the grapes.

A problem with the use of some muscadine pomace extracts in the past was that the solubility of ellagic acid in the extract was undesirably low, particularly in a bronze extract. As shown in WO 2010/014870 and WO 2010/014873, the inventors developed a method to promote the solubility of ellagic acid in a muscadine pomace extract by combining a bronze and purple muscadine pomace extract. The combination of bronze and purple muscadine pomace extract was found to surprisingly increase the solubility of ellagic acid in the combined extract. The solubility of ellagic acid solubility was surprisingly increased even at low ratios of purple to bronze extract (such as a ratio in the range of 0.1 to 10 or 0.3 to 3) in both unconcentrated and concentrated forms. Compositions that contained increased levels of ellagic acid in combination with supplemental resveratrol (from a source other than muscadine) were found to have surprisingly synergistic lipophilic antioxidant activity, particularly as measured by ORAC. The synergistic antioxidant activity in the lipophilic ORAC($ORAC_{lipophilic}$) suggested that the antioxidant activity would be particularly effective in lipophilic environments, such as that found in low density lipoprotein (LDL). In particular examples, the exogenous source of resveratrol was Japanese knotweed extract.

It has now been determined that further synergistic effects can be obtained by combining a resveratrol with a mixture of muscadine pomace extract and an additional source of polyphenols, such as a source of anthocyanins, for example elderberry fruit.

A. Increased Solubility of Ellagic Acid in Combined Bronze and Purple Muscadine Pomace Extracts Determination of the maximum solubility of ellagic acid (which is unique to muscadine grapes) in a muscadine pomace extract allowed extracts to be prepared with enhanced ellagic acid solubility (and thus capture the polyphenol profile of the pomace) which in turn allowed extracts with improved antioxidant activity to be prepared. As disclosed in WO 2010/014870 and WO 2010/014873 (which are incorporated herein by reference), muscadine extracts with improved ellagic acid solubility can be administered either alone or in combination with other compounds in a non-beverage food, a beverage, dietary supplement or a topical ointment. Various methods of making the combined extracts were disclosed, such as combining a bronze muscadine pomace extract with a purple muscadine pomace extract to produce a muscadine pomace extract, wherein the ratio of bronze muscadine pomace extract to purple muscadine pomace extract ranges from 0.1 to 10 (weight to weight), such as 0.3 to 3 (weight to weight). The combined extract could be extracted by separate extraction of bronze and purple muscadine grapes with subsequent combination of the extracts, or by simultaneous extraction of bronze and purple muscadine grapes combined in desired ratios.

In WO 2010/014870 and WO 2010/014873 the inventors determined the antioxidant capacity of the disclosed muscadine pomace extract and a Japanese knotweed extract, standardized to 98% trans-resveratrol, separately and in combination (in either a mixture or dietary supplement) as measured by an ORAC assay. Both hydrophilic antioxidant capacity and lipophilic antioxidant capacity of the samples were measured. These studies demonstrated a strong synergistic lipophilic antioxidant effect of a mixture of the muscadine pomace extract and Japanese knotweed root extract, standardized to 98% trans-resveratrol. The selective synergy exhibited in the lipophilic conditions was unexpected. The muscadine extract utilized in the composition can be a natural extract and can vary by species and extraction process while retaining synergistic lipophilic antioxidant activity. In particular examples specifically disclosed ratios of muscadine polyphenols to resveratrol are present in the composition.

A composition containing Japanese knotweed extract, standardized to 98% trans-resveratrol, in combination with a muscadine pomace extract has improved lipophilic antioxidant capacity when compared to the sum of the lipophilic antioxidant capacities contributed by the individual extracts contained in the composition. Oxidative processes occurring in lipophilic environments are thought to initiate the pathogenesis of many disease states, such as low density lipoprotein (LDL) oxidation in atherosclerosis and obesity-induced insulin resistance in Type II diabetes. Moreover, oxidation of dietary lipids within the gastrointestinal tract leads to absorption of cytotoxic and genotoxic lipid peroxidation products such as malondialdehyde (MDA). Lipophilic antioxidants have been found to be effective in reducing various types of skin damage by inhibiting lipid peroxidation and the products produced by lipid peroixdation, such as cross-linking agents. Since oxidative stress is a central mechanism underlying normal aging, the disclosed antioxidant compositions are useful for inhibiting free radical production or activity, thereby slowing processes associated with cellular aging.

The applicant's incorporated WO 2010/014870 and WO 2010/014873 disclose muscadine pomace extract compositions having improved antioxidant activity. The muscadine pomace extract compositions were disclosed as components of a non-beverage food, a beverage, a liquid or solid dietary supplement or a topical ointment. Methods of producing the disclosed compositions include combining a muscadine (*Vitis rotundifolia*) pomace extract having a polyphenol content of at least 2% and trans-resveratrol from a source other than muscadine with a minimum purity of at least 5%, wherein a ratio of muscadine polyphenols to trans-resveratrol is in the range of 0.1/1 to 10/1 (weight to weight). Methods of producing the disclosed compositions include combining a muscadine (*Vitis rotundifolia*) pomace extract having a polyphenol content of at least 2% and trans-resveratrol from a source other than muscadine with a minimum purity of at least 5%, wherein a ratio of muscadine pomace extract to trans-resveratrol is in the range of 0.2/1 to 50/1 (weight to weight), such as 5/1 to 50/1 (weight to weight) including 20/1 to 50/1 (weight to weight), such as 18 to 1 (weight to weight), thereby producing a muscadine pomace extract and trans-resveratrol mixture with antioxidant activity. In some embodiments, the ratio of bronze to purple muscadine pomace extract ranges from 0.1 to 10, such as 0.3 to 3, as described in further detail below.

B. Muscadine Pomace Extracts

Muscadine pomace extracts disclosed in WO 2010/014870 and WO 2010/014873 are derived from bronze muscadine pomace and purple muscadine pomace. In some embodiments, the ratio of bronze muscadine pomace extract to purple muscadine pomace extract in the muscadine pomace extract range from 0.1 to 10 (weight to weight), such as 0.3 to 3 (weight to weight). For example, the ratio of bronze muscadine pomace extract to purple muscadine pomace extract is about 2.75 to about 1 (weight to weight), 2.5 to about 1 (weight to weight), about 2.25 to about 1 (weight to weight), about 2 to about 1 (weight to weight), about 1.5 to about 1 (weight to weight), or about 1 to about 1 (weight to weight). In other examples, the ratio is about 10 to about 1, about 7.5 to about 1, or about 5 to about 1. As used herein the term "about" is defined as ±0.5. In a particular example, the ratio of bronze muscadine pomace extract to purple muscadine pomace extract is about 2.25 to about 1 (weight to weight).

In certain embodiments, the muscadine (*Vitis rotundifolia*) pomace extract has a polyphenol content of at least 2%. For example, the polyphenol content is at least 3%, at least 3.5%, at least 4%, at least 4.5%, at least 5%, at least 6%, at least 8%, at least 10%, at least 12%, or at least 14%. In a particular example, the muscadine (*Vitis rotundifolia*) pomace extract has a polyphenol content of about 4%.

In some embodiments, the disclosed muscadine pomace extracts include 20% to 50% solids, such as at least 25%, at least 30%, at least 35%, at least 37%, at least 40%, at least 42%, at least 44%, at least 46% or at least 48%, in a liquid. In a particular example, the extract includes about 40% solids in a liquid.

C. Methods of Making Muscadine Pomace Extracts

WO 2010/014870 and WO 2010/014873 also disclose methods of making muscadine pomace extracts wherein the ratio of bronze muscadine pomace extract to purple muscadine pomace extract ranges from 0.1 to 10 (weight to weight), such as 0.3 to 3 (weight to weight). Although the extracts can be obtained by any extraction method, such as pressing under pressure or extracting with a solvent, particular examples are solvent extracted, for example with alcohol, water (such as heated water), or a combination of alcohol and water. In one disclosed embodiment, muscadine pomace extracts are prepared by simultaneously extracting bronze muscadine pomace and purple muscadine pomace that are present in proportions that yield desired ratios of bronze and purple extract. In other examples, the bronze muscadine pomace extracts and purple muscadine pomace extracts are prepared separately. For example, bronze muscadine pomace and purple muscadine pomace are separately extracted with water, preferably heated water.

The extract can further be fermented to remove extracted sugars. In one example, fermentation is performed following extracting the bronze muscadine pomace and purple muscadine pomace but prior to combining the bronze muscadine pomace extract with the purple muscadine pomace extract to produce a disclosed muscadine pomace extract. In other examples, fermentation is performed after combining the bronze muscadine pomace extract with purple muscadine pomace extract in the desired post extraction ratio (such as at about a 2:25 to 1 bronze to purple ratio).

Fermentation may be performed by any method known to one of skill in art, including those described herein. For example, yeast and yeast nutrients can be added to the pomace and fermentation continued until the residual sugar content is converted to ethanol. In one example, two pounds of yeast are added per 1000 gallons of 1× (unconcentrated) extract; fermentation is typically complete after three days. In other examples, the amount and/or strain of yeast and duration and temperature of fermentation may vary according to individual methods known to one of skill in art. In some examples, enzymes are used to clarify and/or settle residues or to improve extraction yield in the pomace extracts. Examples of such enzymes include pectinase or a blend of enzymes from *Aspergillus niger* that are commercially available from sources such as Scott Laboratories. These enzymes may be added to the pomace extract before or during fermentation.

In some embodiments, the bronze muscadine pomace extracts and purple muscadine pomace extracts are filtered prior to and/or following fermentation. Filtration can be performed according to general methods known to those of skill in the art. In a particular example, extracts are filtered through sieves of appropriate mesh size, such as USP mesh (typically 120 mesh) or a similar cloth filter (for example filters commercially available from Millipore Corporation).

In certain embodiments, methods of making muscadine pomace extracts further include concentrating the bronze muscadine pomace extract and the purple muscadine pomace extract so that each extract includes 20% to 50% solids, such as at least 25%, at least 30%, at least 35%, at least 37%, at least 40%, at least 42%, at least 44%, at least 46% or at least 48%, in a liquid. In a particular example, the extracts are concentrated so that each extract includes about 40% solids in a liquid. Generally known methods for concentrating samples, including methods for concentrating samples disclosed herein, can be used to concentrate the bronze and purple extracts.

In a particular example, to prepare a muscadine pomace extract at 40% solids, the muscadine pomace extract is dried down into a powder form and re-constituted in water at 40% solids level. Alternatively, a more acceptable commercially approach is concentration by removal of the extraction solvent through evaporation under vacuum using a batch or continuous process. Batch processes involve placing the extract in a vessel under a vacuum of 20-29" of mercury while heating the vessel jacket to provide energy to increase the vapor pressure of the solvent. Solvent vapors are condensed external to the vessel and the rate of condensation controls the temperature of the condensate. The same principles apply to a continuous evaporation process but with the advantage that the condensate is exposed to elevated temperatures for a shortened period of time. Both processes are applicable to the concentration of a muscadine pomace extract described herein.

In particular embodiments, bronze and purple pomace are extracted separately and each of the extracts is filtered prior to combining the bronze and purple pomace extract at the desired ratio. In some examples, this method can further include fermenting the combined muscadine pomace extract to remove extracted sugars. In one example, more than one filtering step is used, for example by filtering the extract prior to and following fermentation. In some examples, the method can further include concentrating the extract, as described herein. For example, the extract is concentrated by removal of the extraction solvent through evaporation under vacuum.

D. Compositions with Antioxidant Activity

Disclosed herein are compositions with improved antioxidant activity. In some disclosed embodiments, the compositions includes a muscadine (*Vitis rotundifolia*) pomace extract having a polyphenol content of at least 2% and trans-resveratrol from a source other than muscadine grapes (such as a Japanese knotweed root extract) with a minimum purity of at least 5%, wherein a ratio of muscadine polyphenols to trans-resveratrol is in the range of 0.1/1 to 10/1 (weight to weight), thereby providing a composition with antioxidant activity.

In some examples, the composition includes a muscadine (*Vitis rotundifolia*) pomace extract having a total polyphenol content of at least 3%, at least 3.5%, at least 4%, at least 4.5%, at least 5%, at least 6%, at least 8%, at least 10%, at least 12% or at least 14% and trans-resveratrol from a source other than muscadine grapes with a minimum purity of at least 5%, at least 10%, at least 25%, at least 50%, at least 60%, at least 70%, at least 75%, at least 80%, at least 85%, at least 90%, at least 95%, at least 97%, or at least 98%. In a particular example, the composition includes a muscadine (*Vitis rotundifolia*) pomace extract with a polyphenol content of about 4% and trans-resveratrol from a source other than muscadine grapes with a minimum purity of at least 98%.

In some embodiments, the composition includes a muscadine pomace extract with 20% to 50% solids, such as at least 23%, at least 25%, at least 30%, at least 35%, at least 37%, at least 40%, at least 42%, at least 44%, at least 46% or at least 48%, in a liquid. In a particular example, the extract includes about 40% solids in a liquid.

In other embodiments, the resveratrol includes at least 5% trans-resveratrol, such as at least 10% trans-resveratrol, at least 20% trans-resveratrol, at least 30% trans-resveratrol, at least 40% trans-resveratrol, at least 50% trans-resveratrol, at least 55%, at least 60%, at least 70%, at least 75%, at least 80%, at least 85%, at least 90%, at least 95%, at least 97%, or at least 98% trans-resveratrol. In particular embodiments, resveratrol includes at least 50% trans-resveratrol, such as at least 55%, at least 60%, at least 70%, at least 75%, at least 80%, at least 85%, at least 90%, at least 95%, at least 97%, or at least 98% trans-resveratrol extracted from Japanese Knotweed (*Polygonum cuspidatum*) root. It is contemplated that other trans-resveratrol sources can be used in the disclosed composition including synthetic trans-resveratrol.

In certain embodiments, the disclosed antioxidant composition has a ratio of muscadine polyphenols to trans-resveratrol of at least 0.1 to 1 (weight to weight), such as, 0.25 to 1, 0.5 to 1, 0.6 to 1, 0.65 to 1, 0.7 to 1, 0.75 to 1, 0.8 to 1, 0.9 to 1 or 1 to 1 (weight to weight). In other embodiments, the ratio of muscadine polyphenols to trans-resveratrol may be as high as 10 to 1 (weight to weight), such as 2 to 1, 3 to 1, 4 to 1, 5 to 1, 7.5 to 1 or 9 to 1 (weight to weight). In a particular example the disclosed antioxidant composition has a ratio of muscadine polyphenols to trans-resveratrol of 0.75 to 1 (weight to weight).

In certain embodiments, the disclosed antioxidant composition has a ratio of muscadine pomace extract to trans-resveratrol ranging from 0.2/1 to 50/1 (weight to weight), such as 0.5 to 1, 1 to 1, 5 to 1, 10 to 1, 15 to 1, 20 to 1, 22 to 1, 25 to 1, 30 to 1, to 1, 40 to 1, or 45 to 1 (weight to weight).

In some embodiments, the disclosed compositions with antioxidant activity have a total ORAC of at least 21 μmole Trolox Equivalents per mg polyphenol (μmoleTE/mg polyphenol), such as at least 22 μmoleTE/mg polyphenol), at least 24 μmoleTE/mg polyphenol), at least 26 μmole μmoleTE/mg polyphenol, at least 28 μmoleTE/mg polyphenol, or at least 30 μmoleTE/mg polyphenol. In one example, a disclosed composition has a total ORAC of 24 μmoleTE/mg polyphenol.

Some examples of the disclosed compositions further include an elderberry extract, a purple carrot extract, an excipient (such as glycerin, sorbitol, colloidal silicon dioxide, or a natural flavoring additive) or a combination thereof. For example, the elderberry extract and purple carrot extract can be included to provide color to the composition or for additional antioxidant activity.

In other embodiments of the method, the antioxidant composition is further combined with polyphenols (such as anthocyanins) from a source other than muscadine, for example by adding elderberry fruit extract to the antioxidant composition. In particular embodiments the components are combined so that the antioxidant composition includes at least 10% polyphenols, for example up to 35% polyphenols, such as 12-32%. In particular disclosed examples, in which an elderberry extract is providing polyphenols such as anthocyanins, the elderberry extract provides at least one-fourth of the total polyphenols in the muscadine/elderberry mixture, for example one-third to two-thirds of the total polyphenols and at least one fifth, for example 25% to 90% of the anthocyanins in the muscadine/elderberry mixture.

Any of the disclosed compositions can be provided in a non-beverage food, a beverage, or a liquid or solid dietary supplement. In some examples, the disclosed compositions are provided as a beverage. The compositions herein (particularly the food, beverage and dietary supplement compositions) can be fortified with one or more nutrients, especially one or more vitamins and/or minerals. Non-limiting examples of such vitamins and minerals include iron, zinc, copper, calcium, phosphorous, niacin, thiamin, folic acid, pantothenic acid, iodine, vitamin A, vitamin C, vitamin B2, vitamin B3, vitamin B6, vitamin B12, vitamin D, vitamin E, and vitamin K. Commercially available sources of the vitamins and minerals may also be included in the present compositions.

In some examples, food and beverage compositions can also include one or more dietary fibers. By "dietary fiber" is meant complex carbohydrates resistant to digestion by mammalian enzymes, such as the carbohydrates found in plant cell walls and seaweed or produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose or cellulose flour can also be used. Naturally occurring fibers include fiber from whole citrus peel, citrus albedo, sugar beets, citrus pulp and vesicle solids, apples, apricots, and watermelon rinds.

Beverage acidity can be adjusted to and maintained within a desired range by conventional methods such as the use of food grade acid buffers. Typically, beverage acidity within the above recited ranges is a balance between maximum acidity for microbial inhibition and optimum acidity for the desired beverage flavor. In some examples, the beverage compositions has a pH from about 2 to about 8, such as from about 2 to about 4.5 or about 2.7 to about 4.2.

Organic as well as inorganic edible acids may be used to adjust the pH of the beverage composition. The acids can be present in their undissociated form or as their respective salts, including potassium or sodium hydrogen phosphate, potassium or sodium dihydrogen phosphate salts. In some examples, the acids include citric acid, malic acid, fumaric acid, adipic acid, phosphoric acid, gluconic acid, tartaric acid, ascorbic acid, acetic acid, phosphoric acid, pyruvic acid or mixtures thereof. The acidulant can also serve as an antioxidant to stabilize beverage components. Examples of commonly used antioxidant include but are not limited to ascorbic acid, EDTA (ethylenediaminetetraacetic acid), and salts thereof.

E. Methods of Making Muscadine Compositions with Antioxidant Activity

Muscadine pomace extract compositions with antioxidant activity can be made by a variety of methods. For example, the compositions can be prepared by dissolving, dispersing, or otherwise mixing all components singularly or in suitable combinations together and in water where appropriate, and agitating the mixture with a mechanical stirrer until all of the ingredients have been solubilized or adequately dispersed. Separate solutions or mixtures may be combined. The final mixture can optionally be pasteurized or filled aseptically under appropriate process conditions to promote shelf-stability.

In some examples, a muscadine (Vitis rotundifolia) pomace extract having a polyphenol content of at least 2% is combined with resveratrol from a source other than muscadine wherein the resveratrol has a minimum purity of at least 5% (such as at least 10%, at least 20%, at least 30%, at least 40%, at least 50%, at least 60%, at least 70%, at least 80%, at least 90%, at least 95%, at least 98% or at least 99%) wherein a ratio of muscadine polyphenols to trans-resveratrol is in the range of 0.1/1 to 10/1 (weight to weight), for example 0.75 to 1, thereby producing a muscadine pomace extract and trans-resveratrol mixture with antioxidant activity. The disclosed methods can further include preparing the muscadine pomace extract prior to combining the muscadine pomace extract with trans-resveratrol.

In one particular example, the muscadine pomace extract is prepared by combining a bronze muscadine pomace extract with a purple muscadine pomace extract. In other examples, the muscadine pomace extract is prepared by extracting a mixture of bronze muscadine pomace and purple muscadine pomace simultaneously from a mixture of bronze and purple muscadine grapes. The muscadine pomace extract can be prepared according to known methods such as crushing, pressing, extraction, filtering (several times), and concentration of the extract by vacuum evaporation followed by freezing. In one example, only water is utilized for the extraction process and no additional components (such as solvents, carriers, or preservatives) are added to the extract itself. The process is performed under conditions to preserve the polyphenolic compounds while reducing the presence of other molecules, for example, the majority of sugars. In other examples, ethanol or a mixture of ethanol and water are utilized for the extraction process. In particular examples, the extraction process can further include the use of enzymes for clarifying or facilitating extraction. For example, a blend of enzymes from Aspergillus niger or pectinase can be used for these purposes. Commercial examples include Scottzyme KS and ScottzymePEC5L from Scott Laboratories.

In other examples, the compositions are prepared by utilizing muscadine pomace extracts with a total phenol concentration of at least 2%. For example, commercially available muscadine extracts with a total phenol concentration of at least 2% can be used to prepare the disclosed compositions with antioxidant activity.

In a particular example, the composition with antioxidant activity is prepared by combining a muscadine pomace extract and resveratrol with an elderberry extract, a purple carrot extract, an excipient (such as glycerin, sorbitol, colloidal silicon dioxide, or a natural flavoring additive) or a combination thereof.

Another disclosed embodiment is a method of making an antioxidant composition by combining a muscadine (Vitis rotundifolia) pomace extract with resveratrol from a source other than muscadine, wherein a ratio of muscadine pomace extract polyphenols to trans-resveratrol is in the range of 0.1/1 to 10/1 (weight to weight), and the resulting composition has a polyphenol content of at least 2%. The muscadine pomace extract may optionally be concentrated prior to combining it with the resveratrol from a source other than muscadine. In some examples the muscadine pomace extract and resveratrol are combined with polyphenols from a source other than muscadine (such as a source of anthocyanins), for example from one or more of an extract of elderberry, black currant, blueberry, black raspberry, red raspberry, blackberry, bilberry, cloudberry, chokeberry, gooseberry, grape or purple carrot.

In particular embodiments, the method includes combining a mixture of bronze and purple muscadine pomace extract and elderberry fruit extract having a polyphenol content of at least 5% with a Japanese Knotweed root extract. In certain examples the Japanese Knotweed root extract is at least 98% resveratrol, and/or the muscadine pomace extract is a mixture of bronze and purple muscadine pomace extract. In some embodiments of the method the bronze and purple muscadine pomace extracts are combined or otherwise present in a ratio that ranges from 0.1 to 10.

In another embodiment, bronze and purple muscadine pomace extract are solvent extracted, either separately or together, to obtain a mixture of bronze and purple muscadine pomace extract containing solubilized ellagic acid, then the mixture of bronze and purple muscadine pomace extract are concentrated, for example to a solids content of at least 40% The concentrated bronze and purple muscadine pomace extract mixture is combined with resveratrol from a source other than the muscadine pomace extract to obtain an antioxidant mixture, such that the ratio of muscadine pomace extract polyphenols to trans-resveratrol in the antioxidant mixture is in a range of 0.1/1 to 10/1 (weight to weight), and the resulting antioxidant composition has a polyphenol content of at least 2%.

In other embodiments of the method, the antioxidant composition is further combined with polyphenols (such as anthocyanins) from a source other than muscadine, for example by adding elderberry fruit extract to the antioxidant composition. In particular embodiments the components are combined so that the antioxidant composition includes at least 10% polyphenols, for example up to 35% polyphenols, such as 12-32%.

In making a ready-to-drink composition, a beverage concentrate may optionally be formed first. One method to prepare the concentrate form of the beverage composition is to start with less than the required volume of water that is used in the preparation of the beverage composition. Another method is to partially dehydrate the finally prepared beverage compositions to remove only a portion of the water and any other volatile liquids present. Dehydration can be accomplished in accordance with well-known procedures, such as evaporation under vacuum. The concentrate can be in the form of a relatively thick liquid. A syrup is typically formed by adding suitable ingredients such as electrolytes or emulsions to the beverage concentrate. The syrup is then mixed with water to form a finished beverage or finished beverage concentrate.

Dry mixtures of the disclosed compositions can be prepared by blending the proper amounts and ratios of all the required dry ingredients together. Alternatively, the beverage compositions can be dehydrated to give the essentially dry mixture. The essentially dry mixture (for example a powder, granules or tablets) can later be dissolved in a proper amount of water, carbonated or non-carbonated, to make the final drinkable beverage or taken in conjunction with water.

As a form of foods, the disclosed compositions can be formulated to any optional form, such as a granule state, a grain state, a paste state, a gel state, a solid state, or a liquid state. Additional substances can be included, such as a binder, a disintegrant, a thickener, a dispersant, a reabsorption promoting agent, a tasting agent, a buffer, a surfactant, a dissolution aid, a preservative, an emulsifier, an isotonicity agent, a stabilizer or a pH controller. In particular examples, when the disclosed compositions are prepared as foods for preservation of health (including, but not limited to improving skin quality), functional foods, etc., it is preferred to contain the active ingredients of the present compositions and extracts (e.g., muscadine pomace extract, resveratrol, and elderberry extract) in such an amount that the predetermined effects of the present disclosure are shown to be sufficient to provide antioxidant activity.

F. Methods and Kits for Inhibiting (for Example Preventing) Cellular Aging

The disclosed compositions have surprisingly synergistic lipophilic antioxidant activity. It is known that oxidative stress is a central mechanism underlying normal aging. It is also known that lipophilic antioxidants are capable of inhibiting various types of skin damage. Based on these observations, methods are disclosed for inhibiting cellular aging, for example by inhibiting or reducing free radical production or activity. In one example, a dose of the composition is administered to a subject in need of antioxidant activity and the dose is sufficient to inhibit or reduce one or more processes associated with cellular aging, such as free radical formation or activity in the subject.

The composition is also useful to treat any disorder associated with oxidative stress. The present extracts and combined compositions can be used to reduce, prevent or treat oxidative stress associated with the pathogenesis of chronic inflammatory diseases such as diabetes, cancer, atherosclerosis and other cardiovascular disease as well as with degenerative diseases of the central nervous system or brain, such as Alzheimer's disease and Parkinson's disease.

In some examples of the method an antioxidative effective amount of the composition is administered to a subject to increase $ORAC_{lipophilic}$ in the subject. In other embodiments, the effective amount of the composition increases one or more of mitochondrial oxygen consumption, lipophilic ORAC, mitochondrial biogenesis, or expression of mitochondrial biogenesis or antioxidant genes. Examples of the mitochondrial biogenesis genes are one or more of NRF1, SIRT3, COX, and examples of the antioxidant genes include one or more of NRF2, NQO-1, and GST-P1. In some embodiments of the method, a subject is selected who is in need of increased mitochondrial biogenesis and/or antioxidant activity (such as antioxidant activity in lipophilic tissue), and the composition is administered to the subject to increase any of these activities. The composition may be administered in an ingestible form, such as those described herein, that includes a muscadine (*Vitis rotundifolia*) pomace extract derived from bronze muscadine pomace and purple muscadine pomace.

Other embodiments of the methods improve skin quality by inhibiting or reducing free radical formation or activity in a skin cell by applying a solution or topical ointment containing a muscadine pomace extract either alone or in combination with additional active ingredients, including without being limited to resveratrol. In one example, the solution or topical ointment includes a disclosed muscadine pomace extract without resveratrol. In another example, the solution or topical ointment includes both a disclosed muscadine pomace extract and resveratrol, such as a muscadine pomace extract with a ratio of muscadine polyphenols to resveratrol of about 0.75 to 1 (weight to weight). In yet other examples, the composition includes polyphenols (such as anthocyanins) from a source other than muscadine, for example from elderberry fruit extract. The method can be performed by a clinician or other healthcare provider, or can be designed for home use. The method can reduce the appearance of skin changes associated with aging, visibly reduce human skin wrinkles, and improve the textural quality of skin. Compositions and kits for improving skin quality are also provided that can include a disclosed composition (including oral or topical) with antioxidant activity or muscadine extract and one or more additional anti-aging compositions, such as one or more additional antioxidants.

Any skin surface (such as the epidermis of the skin or any facial surface) can be treated using the disclosed methods. Examples of skin surfaces that can be treated are periorbits, lips, cheeks, nasolabial folds, forehead, neck, upper lip rhytides, stomach, neck, back, chest, hands, legs, feet, or any combination thereof. The composition can be applied to any facial and/or body surface area, such as the chest and neck. More than one skin surface can be treated during the same treatment period. In particular examples a liquid or cream form of the disclosed composition or extract is applied substantially evenly across the surface of the skin to form a layer of the composition or extract on the skin.

Muscadine pomace extract compositions may be included in skin quality improvement kits for use in the home or by a clinician such as a physician or aesthetician. The kit can include applicators to apply the composition to skin, and instructions for use. The instructions can be written or in a digital formal (such as a videotape, DVD or CD) for use with electronic devices such as computers, CD players, mp3 players or DVD players and the like. In another example, the kit is suitable for use in the home. In some examples, the kit includes the muscadine composition and one or more additional anti-aging compounds, such as another antioxidant (e.g., vitamin C, vitamin E, selenium and/or beta-carotene), either in two separate containers or as a single composition in a single container.

When used at home, a measured quantity of the composition or extract is applied to a target area, such as the surface of the skin, by the use of an applicator, such as a sponge or cloth, or by the use of one or more fingers, to provide an even layer of the composition or extract on the skin surface. The composition or extract is retained on the skin a specified period of time to be passively absorbed into the skin surface. Absorption can be facilitated by gently rubbing the composition into the skin surface with the fingertips. This process can be performed as described twice daily, daily, every other day, biweekly, weekly, every other week, or monthly, or for some other interval, such as once every 3 to 5 days. Skin quality is improved by reversing, slowing the progression of, reducing the appearance of, or preventing skin changes associated with natural or innate aging. As used herein, "prevent" and variations thereof refer to any degree of delaying the onset of skin changes. For example, improving skin quality includes the reversal, slowing the progression of, or prevention of skin changes associated with free radical formation and activity.

Skin changes treatable by practicing the methods and using the kits disclosed herein include, for example, wrinkles (including, but not limited to, human facial wrinkles), creases, furrows, folds and fine lines, deepening of skin lines, thinning of skin, preventing or reducing scarring, yellowing of the skin, mottling, hyperpigmentation, appearance of pigmented and/or non-pigmented age spots, leatheriness, loss of elasticity, loss of recoilability, loss of collagen fibers, abnormal changes in the elastic fibers, deterioration of small blood vessels of the dermis, formation of solar increased visible vasculature on the skin surface, and combinations thereof.

Improving skin quality includes decreasing, reducing, and/or minimizing one or more of the skin changes discussed above. Improving skin quality can result in the skin having a more youthful appearance, or having a smoother, more hydrated (less dry), or less scaly appearance. For example there may be a reduction in roughness, dryness, or scaliness, the effacement and improvement of lines and wrinkles, or enhanced turgor and tonicity with the observed desired effects of lifting and tightening. The texture of the skin can be improved, such as softness, suppleness, and smoothness, leading to enhancement of luster, clarity and brightness. Additional and important qualities of the skin that can be subjectively and objectively measured include, but are not limited to skin laxity, or conversely skin tightness, and the presence and degree of textural fine lines and coarser lines within the skin.

These are the same qualities by which the external aspects of appearance (for example, aging of skin) are judged. Improvement in these qualities by the method of treatment and kits disclosed herein result in a benefit based on visual judgment of appearance. Changing a quality of the skin by the methods disclosed herein lessens the appearance of aging of the skin.

Desired benefits may include not only physiologic benefit to the skin, but therapeutic and pharmacologic benefits, such as possible malignancy prevention and treatment, whether by chemoprevention or enhancement of photodynamic therapy. Benefits may also include acne treatment and suppression, by including compositions which suppress sebaceous glandular activity G. Compositions with a Pharmaceutical Carrier The disclosed muscadine pomace extracts and compositions can be useful for inhibiting one or more oxidative processes, such as free radical formation associated with cellular events such as cellular aging. The compositions can include a pharmaceutical carrier and at least one disclosed muscadine pomace extract either alone or in combination with resveratrol from a source other than muscadine. In some embodiments the composition also contains a supplemental source of polyphenols from other than muscadine. The pharmaceutical carrier can be for pharmaceutical or non-pharmaceutical uses, for example a use that may or may not require regulatory approval prior to sale for a particular purpose, such as a drug. However, a "pharmaceutical composition" as used herein refers to a composition that contains a pharmaceutically compatible carrier.

Formulations for such compositions are well known in the art. For example, *Remington's Pharmaceutical Sciences*, by E. W. Martin, Mack Publishing Co., Easton, Pa., 19th Edition, 1995, describes exemplary formulations (and components thereof) suitable for pharmaceutical delivery of the active ingredients disclosed herein. The pharmaceutical compositions can be formulated for use in human or veterinary medicine. Particular formulations of a disclosed pharmaceutical composition may depend on the mode of administration (e.g., oral, topical or parenteral) and/or on the condition to be treated (e.g., free radical production or activity). In some embodiments, formulations include a pharmaceutically acceptable carrier in addition to at least one active ingredient, such as a muscadine pomace extract.

The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions such as powder, pill, tablet, or capsule forms conventional non-toxic solid carriers can include pharmaceutical grades of mannitol, lactose, starch, or magnesium stearate. In addition to biologically neutral carriers, pharmaceutical compositions to be administered can optionally contain minor amounts of non-toxic auxiliary substances or excipients, such as wetting or emulsifying agents, preservatives, and pH buffering agents and the like; for example, sodium acetate or sorbitan monolaurate. Other nonlimiting excipients include, nonionic solubilizers, such as cremophor, or proteins, such as human serum albumin. Oral formulations may be liquids such as syrups, solutions or suspensions or solid such as powders, pills, tablets, or capsules.

H. Administration of Disclosed Extracts and Compositions

In a particular example, a composition is administered orally to a mammalian subject, such as a human, in the form of a non-beverage food, a beverage or a dietary supplement. In another example, a composition is administered topically to a skin surface of a mammalian subject, such as a human.

The therapeutically effective amount of the agents administered can vary depending upon the desired effects and the subject to be treated. In one example, the method includes daily administration of at least 1 mg of the composition to the subject (such as a human subject). For example, a human can be administered at least 1 g or at least 10 g of the composition daily, such as 1 g to 5 g daily, 5 g to 10 g daily, for example 7 g daily. In one example, the subject is administered at least 5 g of the composition including muscadine pomace extract and resveratrol. In other examples, the subject is administered at least 6.3 g orally of such composition. The dosage can be administered in divided doses (such as 2, 3, or 4 divided doses per day), or in a single dosage daily.

In particular examples, the subject is administered the therapeutic composition on a multiple daily dosing schedule, for example on at least two consecutive days, 10 consecutive days, and so forth, and may continue for a period of weeks, months, or years. In one example, the composition is administered daily for a period of at least 30 days, such as at least 2 months, at least 4 months, at least 6 months, at least 12 months, at least 24 months, or at least 36 months.

The subject matter of the present disclosure is further illustrated by the following non-limiting Examples.

EXAMPLES

Example 1

Determination of Ellagic Acid Solubility in Muscadine Pomace Extracts

This example illustrates the effects of various specific ratios of bronze to purple pomace extracts on ellagic acid solubility, in both a non-concentrated and a concentrated extract. The mixture of bronze and purple extract increases the ellagic acid solubility.

Separate fermented bronze and purple pomace extracts were heated and then mixed in the ratios provided in Table 1 at a total volume of 100 ml.

TABLE 1

Various Ratios of Bronze/Purple Pomace extracts at 1X concentration

| Bronze (mls) | Purple (mls) |
|---|---|
| 75 | 25 |
| 65 | 35 |
| 50 | 50 |
| 25 | 75 |

The resulting extract mixtures were at a 1× concentration since no concentration of the separate bronze and purple pomace extracts had taken place. A 1× concentration typically contained about a 2% solids solution (100 grams of solution equal to 2 grams of dry extract). Approximately 20 milliliters of each ratio was transferred into a respective glass test tube and capped with foil. Samples were heated for 30 minutes at 85° C., then removed from the heat source and allowed to come to room temperature. Samples were then filtered through 0.45 µm PTFE filter w/GMF and analyzed via HPLC/MS to determine their content of ellagic acid. Separate bronze and purple muscadine pomace extracts were also analyzed, through the same process, to determine the baseline values of ellagic acid in both the bronze and purple pomace extracts and to determine the content of anthocyanins in the purple pomace extract. The total area of ellagic acid in the samples was then determined by reverse phase HPLC with a UV-VIS detection at 254 nm in tandem with a Ion-Trap mass detector, using extracted ion chromatogram (EIC) at $[M-H]^-=301$ amu.

To prepare various ratios of bronze/purple pomace extracts at 40% solids, separate bronze and purple muscadine pomace extracts at 1× were dried down into a powder form and reconstituted in water to produce a liquid containing 40% solids. These two separate solutions were then mixed into various ratios according to weight (wt) rather than volume. The various ratios evaluated are provided in Table 2A and 2B.

TABLE 2A

Determination of ellagic acid solubility in various Bronze/Purple extract ratios at 1X concentration.

| | Pre-Analysis Conditions (non-filtered) Heat Extract @ 85° C./30 mins. Allow Cool R.T. (1 hour)/Filter/Analyze | | | % Increase Ellagic Acid |
|---|---|---|---|---|
| Sample ID | Ellagic Acid Relative µg/ml Experimental | Ellagic Acid Relative ug/ml Expected | Anthocyanins Relative µg/ml Extrapolated | Relative µg/ml Experimental vs. Expected |
| Bronze Extract @ 1X | 29.53 | | | |
| Purple Extract @ 1X) | 77.81 | | 472.50 | |
| 25:75 Purple/Bronze Ratio @ 1X | 43.43 | 41.60 | 118.12 | 4.40 |
| 35:65 Purple/Bronze Ratio @ 1X | 51.11 | 46.43 | 165.37 | 10.07 |
| 50:50 Purple/Bronze Ratio @ 1X | 58.59 | 53.67 | 236.25 | 9.16 |
| 75:25 Purple/Bronze Ratio @ 1X | 72.23 | 65.74 | 354.37 | 9.87 |

TABLE 2B

Determination of ellagic acid solubility in various Bronze/Purple extract ratios at approximately 20X concentration or 40% solids level.

| | Pre-Analysis Conditions (non-filtered) Heat Extract @ 85° C./30 mins. Allow Cool R.T. (1 hour)/Filter/Analyze | | | % Increase Ellagic Acid |
|---|---|---|---|---|
| Sample ID | Ellagic Acid Relative ug/ml Experimental | Ellagic Acid Relative ug/ml Expected | Anthocyanins Relative ug/ml Extrapolated | Relative ug/ml Experimental vs. Expected |
| Bronze Extract @ ~40% solids | 3.00 | | | |
| Purple Extract @ ~40% solids | 26.25 | | 981.42 | |
| 2.25:1 Bronze/Purple Ratio ~40% solids | 12.19 | 10.15 | 301.97 | 20.13 |
| 2:1 Bronze/Purple Ratio ~40% solids | 13.29 | 10.75 | 327.14 | 23.66 |
| 1:1 Bronze/Purple Ratio ~40% solids | 20.01 | 14.62 | 490.71 | 36.80 |

Approximately 10 milliliters of each ratio was transferred into a respective glass test tube and capped with foil. Samples were heated for 30 minutes at 85° C., then removed from the heat source and allowed to come to room temperature. Samples were then filtered through a 0.45 µm PTFE filter w/GMF and analyzed via HPLC/MS to determine their content of ellagic acid. Separate bronze and purple muscadine pomace extracts were also analyzed, through the same process, to determine the baseline values of ellagic acid in both bronze and purple muscadine pomace extracts and to determine the content of anthocyanins in the purple muscadine pomace extract. Validated test method C2505 was used to determine the total area of ellagic acid in the samples, in tandem with a Ion-Trap mass detector using extracted ion chromatogram (EIC) at $[M-H]^-=301$ amu.

Mixing the purple with the bronze muscadine pomace extract increased solubility of solubility of ellagic acid in the mixture. These studies found that a ratio of 65% to 35% bronze to purple pomace extract (volume to volume) was sufficient to promote the maximum solubility of ellagic acid in a mixture of the two pomace extracts at the 1× concentration level. Further, at a 40% solids level, the solubility of ellagic acid continued to increase as the content of purple muscadine pomace extract increased in the mixture. These findings suggest that at a 40% solids level, greater amounts of ellagic acid existed in the solid form, so a higher content of purple pomace extract is useful to fully solubilize all the ellagic acid present in the mixture. These studies also suggest that anthocyanins, such as those contained in the purple muscadine pomace extract, influence the solubility of ellagic acid contained within the bronze muscadine pomace extract.

Example 2

Anti-aging Dietary Supplement and Preparation Thereof

Dietary supplements that can be consumed to prevent or inhibit one or more processes associated with cellular aging are disclosed in WO 2010/014870 and WO 2010/014873, which are incorporated by reference.

The dietary supplement includes instructions regarding dosages. For example, the instructions can indicate that 5 milliliters of a liquid supplement (approximately one teaspoon) can be taken daily before a meal and used as an anti-aging supplement for inhibiting one or more processes associated with cellular aging.

Example 3

Antioxidant Capacity of Muscadine Pomace Extract and Japanese Knotweed Root Extract Mixture This example demonstrates the improved antioxidant capacity of a mixture of Japanese knotweed extract and muscadine pomace extract as measured by an Oxygen Radical Absorbance Capacity (ORAC) assay.

The antioxidant capacity of two botanical extracts separately or in combination was evaluated using the ORAC assay. This assay has been used to measure the antioxidant capacity of a wide range of foods and beverages and is the basis for the data contained in the USDA ORAC database. Both hydrophilic antioxidant capacity and lipophilic antioxidant capacity can be measured by this test.

The following samples were analyzed: (1) Dried/powdered Japanese knotweed root extract standardized to a minimum 98% trans-resveratrol (actual content was 100% trans-resveratrol); (2) Dried/powdered Muscadine pomace extract (2:1 ratio of bronze to purple pomace) containing 14.4% total polyphenol content; and (3) Mixture of the above dried/powdered Japanese knotweed and dried/powdered muscadine pomace extracts in a 1:5.36 (wt:wt) ratio (total polyphenol content was 27.5% of mixture and the ratio of muscadine polyphenols to trans-resveratrol was 0.75 to 1. Hydrophilic, lipophilic and total ORAC values were measured (total ORAC value is the sum of the hydrophilic and lipophilic values) and the results are expressed as μmole Trolox Equivalents per milligram polyphenol (μmoleTE/mg polyphenol). The results are shown in Table 3.

TABLE 3

Hydrophilic, lipophilic and total ORAC values for Samples 1-3 as expressed as μmoleTE/mg polyphenol.

| Sample Extract | $ORAC_{hydrophilic}$ | $ORAC_{lipophilic}$ | $ORAC_{total}$ |
|---|---|---|---|
| (1) Japanese knotweed (100% resveratrol) | 29.85 | 1.46 | 31.31 |
| (2) Muscadine pomace (14.4% polyphenols) | 9.69 | 0.06 | 9.74 |
| (3) Mixture - predicted additivity | 21.19 | 0.86 | 22.05 |
| (3) Mixture - actual value | 21.83 | 4.35 | 26.18 |

As displayed in Table 4, the measured hydrophilic ORAC value of the mixture is similar to the predicted value based on the additive effects of the two extracts. However, the measured lipophilic ORAC value of the mixture is five times greater than the predicted additive value resulting in a 20% increase in the total ORAC value—Table 4 shows the results expressed as ORAC value per gram of material (versus per mg polyphenol as shown in Table 3). As displayed in Table 4, the synergistic effects of the muscadine pomace extract and Japanese knotweed root extract mixture in producing lipophilic antioxidant capacity are maintained when values are expressed as ORAC per gram of material:

TABLE 4

Hydrophilic, lipophilic and total ORAC values for Samples 1-4 as expressed as ORAC value per gram of material.

| Extract Sample | $ORAC_{hydrophilic}$ | $ORAC_{lipophilic}$ | $ORAC_{total}$ |
|---|---|---|---|
| (1) Japanese knotweed (100% resveratrol) | 29,852 | 1,457 | 31,309 |
| (2) Muscadine pomace (14.4% polyphenols) | 1,356 | 8 | 1,364 |
| (3) Mixture - predicted additivity | 5,830 | 236 | 6065 |
| (3) Mixture - actual value | 6,003 | 1,197 | 7200 |

Example 4

Reduction of Oxidative Stress in Human Subjects

This example demonstrates the in vivo efficacy of the antioxidant composition described in Example 3 as assessed in a placebo-controlled clinical trial (as reported in Ghanim et al., *J. Clin. Endocrinol. Metab.* 96:1409-1414, 2011).

The composition contained a mixture of muscadine pomace extract and Japanese knotweed extract to provide 75 mg of muscadine polyphenols and 100 mg of trans-resveratrol per 3 capsule dose. It is known that food consumption (for example in a meal) acutely increases oxidative stress and produces an inflammatory response. For example, it has been shown that consumption of a 900 kcal fast food meal elicits significant increases in reactive oxygen species (ROS) generation in circulating mononuclear cells (MNC) and polymorphonuclear leukocytes (PMN) in healthy normal weight humans (Aljada et al., *Am. J. Clin. Nutr.* 79:682-690, 2004). These changes are attended by elevated expression in MNC of p47phox protein, a subunit of the enzyme, NADPH oxidase, a mediator of ROS generation.

To test the effects of the antioxidant composition in this model of postprandial oxidative stress, a group of 10 healthy subjects (age: 37±4 yrs, BMI 22.6±0.5 kg/m2) were given, in two separate days, a 910 kcal fast food meal with either a single dose (3 capsules) of the antioxidant formulation or placebo (3 capsules) taken 10 minutes before the meal. Blood samples were collected at baseline and at 1, 3 and 5 hours following meal intake. Circulating concentrations of glucose, insulin and lipids were similar after each treatment indicating that the disclosed antioxidant capsules did not alter the digestion/absorption of the meal. However, at one hour after meal consumption, the disclosed antioxidant capsule treatment greatly attenuated the increase in ROS generation in both MNC (15% versus 62% for placebo) and PMN (8% versus 64% for placebo). In addition, meal plus placebo intake caused a significant increase in protein levels of p47phox by 148% over the baseline ($P<0.05$) in MNC whereas meal plus antioxidant capsule intake completely prevented any significant change in MNC p47phox levels ($P<0.05$ with 2-way RMANOVA). Moreover, the DNA binding activity of the anti-oxidative stress transcription factor, Nrf-2, was significantly increased by 150% ($P<0.05$ by RMANOVA and 2-way RMANOVA) over the baseline at 3 hours following the meal plus antioxidant capsule intake compared to the placebo treated group wherein there was actually a decline in the DNA binding activity of this protective transcription factor. Nrf-2 binds to the antioxidant response element (ARE) promoter sequence of multiple genes encoding endogenous antioxidant enzymes (e.g., glutathione-S-transferase) and hence, the increased DNA binding of activity of Nrf-2 following intake of the disclosed antioxidant formulation suggests potential for upregulation of multiple cellular defenses.

Finally, following meal and placebo ingestion there was a significant rise in plasma endotoxin levels by 60% over the baseline at 3 hr (P<0.05) while there was a significant fall in endotoxin concentrations by 28% below the baseline at 1 hour when the meal was consumed with the disclosed antioxidant capsules (P<0.05 using RMANOVA and 2-way RMANOVA). Endotoxin is a powerful inflammatory signal that precipitates the activation of a variety of cytokines that increase oxidative stress.

These results demonstrate novel in vivo antioxidant effects of a mixture of muscadine pomace extract and Japanese knotweed (ratio of muscadine polyphenols to trans-resveratrol of 0.75 to 1) and thus extend the in vitro findings of the synergistic antioxidant capacity of this mixture (Example 3).

Based upon these findings, methods of inhibiting oxidative stress are enabled. For example, the disclosed composition is administered to a subject to inhibit oxidative stress, such as that associated with food consumption, such as meal consumption. In one example, the disclosed composition is administered 30 minutes before or after eating, such as 10 minutes before or after eating food. In a particular example, the composition is administered approximately 10 minutes before eating.

Example 5

Measuring Synergistic Activity of Additional Compositions Containing Muscadine and Elderberry Polyphenols in Altering Mitochondrial Biogenesis, Mitochondrial Activity, and Antioxidant Gene Expression Example 3 demonstrated a strong synergistic effect of the muscadine pomace extract and an additional source of resveratrol, such as Japanese knotweed root extract, as an anti-aging composition in producing lipophilic antioxidant capacity. The selective synergy exhibited in the lipophilic conditions was unexpected whereas only additive effects were observed in hydrophilic conditions. The present findings demonstrate the further unexpected finding that selected synergistic effects on antioxidant gene expression, mitochondrial biogenesis, mitochondrial activity and mitochondrial biogenesis gene expression is produced by adding to the composition polyphenols (such as anthocyanins) from a source other than the muscadine grape or Japanese knotweed extract, for example from elderberry fruit extract. The unexpected synergistic mitochondrial effect of the additional polyphenols, such as that from elderberry fruit extract, was evidenced by an increase in mitochondrial biogenesis as measured by mitochondrial mass, activity, and gene expression.

Mitochondrial mass and function decline with age (Lanza and Nair, *Pflugers Arch.*, 249:277-289, 2010; Lopez-Lluch et al., *Exp. Gerontol.* 43:813-819, 2008; Guarente, *Cell* 132: 171-176, 2008); in humans this has been studied primarily in skeletal muscle (Nair, *Am. J. Clin. Nutr.* 81:953-963, 2005; Short et al., *Proc. Natl. Acad. Sci. USA* 102:5618-5623; 2005, Zahn et al., *PLoS Genet.* 2(7):e115. DOI: 10.1371/journal.pgen.0020115). Treatments that have been shown to extend lifespan, such as caloric restriction, increase mitochondrial mass and activity in skeletal muscle, and selected polyphenols such as resveratrol have been shown to promote mitochondrial biogenesis.

Mitochondrial biogenesis is regulated by many signaling pathways and hormones; the expression of multiple genes and transcription factors is altered during mitochondrial biogenesis (Lopez-Lluch et al., *Exp. Gerontol.* 43:813-819, 2008). Thus, it was also determined if the formulation-induced changes observed in mitochondrial density and activity were associated with changes in the expression of genes involved in mitochondrial biogenesis. Specifically, the gene expression of sirtuin 1 (SIRT1), sirtuin 3 (SIRT3), peroxisome proliferator-activated receptor gamma coactivator-1 alpha (PGC1-α), nuclear respiratory factor 1 (nrf1), and cytochrome c oxidase subunit VIIc1 (COX) was measured because the upregulation of these genes is thought to influence mitochondrial biogenesis.

In addition, the expression of major antioxidant genes was measured, especially nuclear factor (erythroid-derived 2)-related factor 2 (nrf2) and its downstream targets. As described in Example 4 (and in Ghanim et al., *J. Clin. Endocrinol. Metab.* 96:1409-1414, 2011), the resveratrol/muscadine combination blunted postprandial oxidative stress and increased the DNA-binding activity of nrf 2 in humans. The role of nrf 2 as a master coordinator of endogenous antioxidant responses as well as its measured decline during aging suggests that upregulation of this transcription factor suppresses cellular aging. Caloric restriction, for example, increased the expression of nrf2 (Suh et al., *Proc. Natl. Acad. Sci. USA* 101:3381-3386, 2004; Pearson et al. *Proc. Natl. Acad. Sci. USA* 105:2325-2330, 2008; Sykiotis et al., *Curr. Opin. Clin. Nutr. Metab. Care* 14:41-48, 2011). Increased mitochondrial mass and function is expected to increase the generation of radical oxygen species, hence concurrent upregulation of endogenous antioxidant activity via nrf2 and its downstream targets is believed to mitigate the damaging effects of increased oxidative stress. Accordingly, the gene expression of nrf2, NAD(P)H quinone oxido/reductase (NQO-1), glutathione S transferase P1 (GST-P1) and the inflammatory mediator, Toll-like receptor 4 (TLR4) was measured in human muscle cells treated with the individual and combined polyphenol components of a new anti-aging supplement formulation that contained the additional source of polyphenols (for example anthocyanins), in this case, from elderberry fruit extract.

Mitochondrial function (oxygen consumption) was also measured to assess synergistic activity of additional polyphenols in the muscadine/resveratrol mixture.

Formulations Tested

The following formulations (1), (2) and (3) were tested:

(1) Dried powdered Japanese knotweed root extract standardized to a minimum 98% trans-resveratrol (actual content was 100% trans-resveratrol);

(2) A mixture of dried powdered muscadine pomace (mixture of bronze and purple) extract containing 16% total polyphenol content and dried powdered elderberry fruit extract containing 15% total polyphenol content in a 1:1.86 ratio (wt:wt) such that the total polyphenol content was 15.6% wherein muscadine and elderberry polyphenols contributed 36% and 64% of the total polyphenol content, respectively;

(3) A mixture of the above dried powdered Japanese knotweed and dried powdered muscadine pomace extract/elderberry fruit extract mixture in a 1:4.82 (wt:wt) ratio such that the total polyphenol content was 30.1% and the ratio of muscadine/elderberry polyphenols to trans-resveratrol was 0.75 to 1 (wt:wt) wherein trans-resveratrol and muscadine/elderberry polyphenols contributed 57% and 43% to the total polyphenol content, respectively. These three test samples will subsequently be referred to as Samples 1, 2 and 3.

The following Table 5 illustrates for Sample 3 the percentage contributions to total polyphenol content and total resveratrol content from the Japanese knotweed root extract, muscadine pomace extract and elderberry fruit extract mixture. Table 5 also specifies the percent contribution to total anthocyanin content of the muscadine pomace and elderberry fruit extracts in the mixture.

TABLE 5

Polyphenol composition for synergistic stimulation of mitochondrial biogenesis, oxygen consumption, and antioxidant and mitochondrial biogenesis regulatory gene expression in Sample (3).

| Raw material | % contribution to total polyphenol content | % contribution to total anthocyanin content | % contribution to total resveratrol content |
|---|---|---|---|
| Japanese knotweed root extract (98.5% resveratrol) | 57 | 0 | 100 |
| Muscadine pomace extract and elderberry fruit extract mixture | 43 | 100 | 0 |
| Muscadine pomace extract | | 11 | |
| Elderberry fruit extract | | 89 | |
| Total | 100 | 100 | 100 | 100 |

Culturing Human Skeletal Muscle Cells

Human skeletal muscle myoblasts isolated from the rectus abdominus muscle (pooled donors) were inoculated at a density of approximately 10,000 cells/cm$^2$ in growth medium containing DMEM, BSA, fetuin, human epidermal growth factor, dexamethasone, human insulin, penicillin, streptomycin, amphotericin B and glucose) and grown at 37° C. in 5% $CO_2$. When the myoblasts reached ~80-90% confluence, differentiation was initiated by replacing the growth medium with a medium containing DMEM, horse serum, BSA, fetuin, penicliin, streptomycin, amphotericin B and glucose. Cells were incubated in differentiation medium at 37° C. in 5% $CO_2$ and medium changed every two days. By day 6-8 cells fused to form fully differentiated myotubes. Cells were then washed and maintained in serum-free differentiation medium overnight prior to initiation of experimental treatment. The cells were then re-fed serum-free differentiation medium containing the indicated treatments for 48 hours for assessment of mitochondrial biogenesis, oxygen consumption, and gene expression as described below.

Mitochondrial Density Measurement

Mitochondrial density was assessed with the mitochondrial probe NAO for analysis of mitochondrial mass and number by fluorescence (excitation 485 nm and emission 520 nm). Imaging and quantitative data were obtained using an inverted fluorescence microscope linked to a color chilled 3CCD camera and additional quantitative data were obtaining with a fluorescence microplate reader. The intensity of fluorescence was normalized to cellular protein content and data then further normalized to control values at each time point.

Oxygen Consumption Measurement

Real-time oxygen consumption by myotubes was measured using the method of Sun and Zemel (Sun and Zemel, Nutr. Metab. 2009; 6:26 [doi10.1.1186/1743-7075-6-26]). Coverslips containing adherent human myotubes treated with the three samples (described above) were subjected to cell counting to assure that equivalent cell numbers were present in all three treatment groups (~1×10$^6$ cells).

Gene Expression Studies

A total cellular RNA extraction kit was used to extract total RNA from cells and the concentration, purity and quality of the isolated RNA were assessed by measuring the 260/280 ratio (1.8-2.0) and 260/230 ratio (1.9 to 2.0) with a spectrophotometer. Expression of the housekeeping gene, 18S rRNA (18S), and key myocyte target genes including sirtuin 1 (SIRT1), sirtuin 3 (SIRT3), peroxisome proliferator-activated receptor gamma coactivator-1 alpha (PGC1-α), nuclear respiratory factor 1 (NRF1), nuclear factor (erythroid-derived 2)-related factor 2 (NRF2), cytochrome c oxidase subunit VIIc1 (COX), NAD(P)H quinone oxido/reductase (NQO-1), glutathione S transferase P1 (GST-P1) and Toll-like receptor 4 (TLR4) was measured via quantitative real-time PCR. Pooled RNA from each cell type was serial-diluted in the range of 1.5625-25 ng and used to establish a standard curve; total RNA for each unknown sample was also diluted in this range. 18S rRNA quantitation served as an internal housekeeping control gene to ensure that any observed differences were not secondary to differences in efficiency of RNA extraction.

A minimum of 9 independent replicates was utilized for each treatment combination. The data were evaluated for normality of distribution and equality of variance; all data met the standard requirements for normality of distribution and equality of variance and thus were evaluated by analysis of variance (ANOVA) and significantly different group means separated by the least significant difference test.

Human muscle cell cultures were treated for 48 hours with various concentrations of the test Samples 1, 2 and 3.

Results

TABLE 6

Effects of different concentrations of Samples 1-3 on mitochondrial mass in human muscle cells (% Increase).

| Sample | 0.68 µg polyphenols/ml | 2.28 µg polyphenols/ml | 6.8 µg polyphenols/ml |
|---|---|---|---|
| (1) Japanese knotweed root extract (100% resveratrol) | 9.00 | 22.00 | 65.00 |
| (2) Muscadine pomace extract/elderberry fruit extract mixture (1:1.86 wt/wt) | 36.00 | 40.00 | 51.00 |
| (3) Mixture of Japanese knotweed root extract and muscadine pomace/elderberry fruit extract mixture (1:4.82 wt/wt)-predicted additivity | 20.51 | 29.65 | 58.68 |
| (4) Mixture of Japanese knotweed root extract and muscadine pomace/elderberry fruit extract mixture (1:4.82 wt/wt)-actual value | 45.00 | 65.00 | 97.00 |

TABLE 7

Effects of different concentrations of Samples 1-3 on mitochondrial mass in human muscle cells (% Increase/µg polyphenol).

| Sample | 0.68 µg polyphenols/ml | 2.28 µg polyphenols/ml | 6.8 µg polyphenols/ml |
|---|---|---|---|
| (1) Japanese knotweed root extract (100% resveratrol) | 13.24 | 9.65 | 9.56 |

TABLE 7-continued

Effects of different concentrations of Samples 1-3 on mitochondrial mass in human muscle cells (% Increase/μg polyphenol).

| Sample | 0.68 μg polyphenols/ml | 2.28 μg polyphenols/ml | 6.8 μg polyphenols/ml |
|---|---|---|---|
| (2) Muscadine pomace extract/elderberry fruit extract mixture (1:1.86 wt/wt) | 52.94 | 17.54 | 7.46 |
| (3) Mixture of Japanese knotweed root extract and muscadine pomace/elderberry fruit extract mixture (1:4.82 wt/wt)-predicted additivity | 30.30 | 13.03 | 8.63 |
| (4) Mixture of Japanese knotweed root extract and muscadine pomace/elderberry fruit extract mixture (1:4.82 wt/wt)-actual value | 66.18 | 28.51 | 14.26 |

The results shown in Tables 6 and 7 demonstrate that combining resveratrol and a mixture of muscadine pomace and elderberry fruit polyphenols produces greater than predicted additive effects on mitochondrial density whether expressed per concentration or per μg polyphenol. Unexpected synergistic effects (greater than the addition of the individual effects of each component) were observed at all concentrations tested.

TABLE 8

Effects of different concentrations of Samples 1-3 on mitochondrial oxygen consumption in human muscle cells (% Increase).

| Sample | 0.68 μg polyphenols/ml | 2.28 μg polyphenols/ml | 6.8 μg polyphenols/ml |
|---|---|---|---|
| (1) Japanese knotweed root extract (100% resveratrol) | 5.9 | 11.07 | 15.5 |
| (2) Muscadine pomace extract/elderberry fruit extract mixture (1:1.86 wt/wt) | 29.4 | 29.50 | 27.4 |
| (3) Mixture of Japanese knotweed root extract and muscadine pomace/elderberry fruit extract mixture (1:4.82 wt/wt)-predicted additivity | 15.93 | 18.92 | 20.48 |
| (4) Mixture of Japanese knotweed root extract and muscadine pomace/elderberry fruit extract mixture (1:4.82 wt/wt)-actual value | 55.00 | 61.10 | 98.80 |

TABLE 9

Effects of different concentrations of Samples 1-3 on mitochondrial oxygen consumption in human muscle cells (% Increase/μg polyphenol).

| Sample | 0.68 μg polyphenols/ml | 2.28 μg polyphenols/ml | 6.8 μg polyphenols/ml |
|---|---|---|---|
| (1) Japanese knotweed root extract (100% resveratrol) | 8.68 | 4.86 | 2.27 |
| (2) Muscadine pomace extract/elderberry fruit extract mixture (1:1.86 wt/wt) | 43.24 | 12.94 | 4.01 |
| (3) Mixture of Japanese knotweed root extract and muscadine pomace/elderberry fruit extract mixture (1:4.82 wt/wt)-predicted additivity | 23.54 | 8.33 | 3.01 |
| (4) Mixture of Japanese knotweed root extract and muscadine pomace/elderberry fruit extract mixture (1:4.82 wt/wt)-actual value | 80.88 | 26.80 | 14.44 |

The results shown in Tables 8 and 9 demonstrate that the combination of resveratrol plus a mixture of muscadine pomace and elderberry fruit polyphenols produces greater than predicted additive effects on cellular oxygen consumption whether expressed per concentration or per μg of polyphenol. Unexpected synergistic effects (greater than the addition of the individual effects of each component) were observed at all concentrations tested.

One concentration (2.28 μg polyphenols/ml) was selected to examine the effects of each extract alone and in combination on the expression of antioxidant and mitochondrial biogenesis-related genes and transcription factors.

TABLE 10

Effects of Samples 1-3 (at 2.28 μg polyphenols/ml) on antioxidant and mitochondrial gene expression in human muscle cells (% Increase).

| Sample | NRF1 | SIRT3 | COX | NRF2 | NQO-1 | GST-P1 |
|---|---|---|---|---|---|---|
| (1) Japanese knotweed root extract (100% resveratrol) | 33.0 | 113.6 | −34.5 | 15.9 | 78.9 | 18.3 |
| (2) Muscadine pomace extract/elderberry fruit extract mixture (1:1.86 wt/wt) | 13.4 | 106.8 | 19.0 | −19.1 | 61.5 | 1.5 |
| (3) Mixture of Japanese knotweed root extract and muscadine pomace/elderberry fruit extract mixture (1:4.82 wt/wt) - predicted additivity | 24.7 | 110.4 | −11.7 | 1.02 | 71.5 | 11.2 |

TABLE 10-continued

Effects of Samples 1-3 (at 2.28 µg polyphenols/ml) on
antioxidant and mitochondrial gene expression
in human muscle cells (% Increase).

| Sample | NRF1 | SIRT3 | COX | NRF2 | NQO-1 | GST-P1 |
|---|---|---|---|---|---|---|
| (4) Mixture of Japanese knotweed root extract and muscadine pomace/elderberry fruit extract mixture (1:4.82 wt/wt) - actual value | 70.1 | 305.1 | 153.4 | 34.1 | 180.8 | 110.7 |

TABLE 11

Effects of Samples 1-3 (at 2.28 µg polyphenols/ml) on
antioxidant and mitochondrial gene expression
in human muscle cells (% Increase/µg polyphenol).

| Sample | NRF1 | SIRT3 | COX | NRF2 | NQO-1 | GST-P1 |
|---|---|---|---|---|---|---|
| (1) Japanese knotweed root extract (100% resveratrol) | 15.9 | 49.8 | −15.1 | 6.9 | 34.6 | 8.0 |
| (2) Muscadine pomace extract/elderberry fruit extract mixture (1:1.86 wt/wt) | −19.1 | 46.6 | 8.3 | −8.4 | 27.0 | 0.7 |
| (3) Mixture of Japanese knotweed root extract and muscadine pomace/elderberry fruit extract mixture (1:4.82 wt/wt) - predicted additivity | 1.02 | 48.4 | −5.0 | 0.38 | 31.3 | 4.9 |
| (4) Mixture of Japanese knotweed root extract and muscadine pomace/elderberry fruit extract mixture (1:4.82 wt/wt) - actual value | 34.1 | 133.8 | 67.3 | 14.9 | 79.3 | 48.6 |

The results shown in Tables 10 and 11 demonstrate statistically significant synergistic effects of the combined extracts on the expression of antioxidant- and mitochondrial biogenesis-related genes whether expressed per concentration or per µg of polyphenol. Specifically, the expression of NRF1, SIRT3, and COX was dramatically and synergistically (effect was greater than the sum of individual components) increased by the combination of resveratrol with muscadine pomace and elderberry fruit polyphenols whereas no such interactions were observed for the expression of SIRT1 and PGC1-α. Of particular interest are the observed effects on COX gene expression—whereas resveratrol decreased the expression of COX and the muscadine pomace/elderberry fruit extract mixture had a small stimulatory effect on COX gene expression, the combination of both extracts produced a robust upregulation of COX gene expression. These results are unexpected and indicate that the expression of selected genes are altered in quite different manners and magnitudes when acted upon by resveratrol or a mixture of muscadine pomace and elderberry fruit polyphenols individually versus as a combination. Similarly, the effects of the combined extracts exceeded the predicted additive effects of the separate extracts on the expression of antioxidant genes NRF2, NQO-1, and GST-P1 whereas no such effect was observed for TLR4. The synergism between extracts was especially pronounced for GST-P1 where a tenfold greater than additive response was measured. Moreover, similar to the gene expression of COX described above, resveratrol and the mixture of muscadine pomace and elderberry fruit polyphenols produced opposite effects on the expression of NRF2 such that the predicted additive effects would have been no change as a result of antagonism; however, the combination of resveratrol with muscadine and elderberry fruit polyphenols unexpectedly produced significant upregulation of NRF2 gene expression.

Example 6

Effect of Elderberry Fruit Extract on Ellagic Acid Solubility in Muscadine Pomace Extract As shown in Example 1, the addition of purple pomace extract to bronze pomace extract enhanced the solubility of ellagic acid contained within the bronze pomace extract. This effect was considerably greater in extracts that were concentrated to the 40% solids level (versus 2% solids level). These findings suggested that the addition of anthocyanins from the purple muscadine pomace extract was beneficial for increasing ellagic acid solubility in bronze muscadine pomace extracts containing high concentrations of ellagic acid.

Elderberry fruit extract contains significant amounts of anthocyanins (but no ellagic acid) and thus experiments were performed to determine whether the soluble ellagic acid content within a muscadine pomace extract (bronze and purple pomace mixture) is influenced by the addition of anthocyanins from elderberry fruit extract. This example shows that soluble ellagic acid content within a muscadine pomace extract is significantly increased by the addition of elderberry fruit extract presumably owing to its anthocyanin content.

Ellagic acid concentrations were measured in (1) dried powdered muscadine pomace extract (2:1 ratio of bronze to purple pomace) and (2) a mixture of the above muscadine pomace extract and dried powdered elderberry fruit extract (containing 6.5% anthocyanins) in a 1:1.86 ratio (wt:wt). Solutions of each sample were prepared at various concentrations to provide 40%, 20%, 10%, and 2% solids. Each solution was heated for 30 minutes at 85° C., removed from the heat source and allowed to reach to room temperature (complete by 1 hour). Samples were then filtered through 0.45 µm PTFE filter w/GMF and analyzed via HPLC/MS to determine their content of soluble ellagic acid. Total area of ellagic acid was assessed by reverse phase HPLC with UV-VIS detection at 254 nm in tandem with a Ion-Trap mass detector, using extracted ion chromatogram (EIC) at [M-H]⁻=301 amu. The results are shown in Table 12.

TABLE 12

Effect of elderberry fruit extract (anthocyanins) on soluble ellagic acid content in muscadine pomace extract.

| | Soluble ellagic acid content (µg/ml) | | | |
|---|---|---|---|---|
| % solids | Muscadine pomace extract (measured) | Muscadine pomace extract/elderberry fruit extract mixture (expected) | Muscadine pomace extract/elderberry fruit extract mixture (measured) | % increase over predicted |
| 40 | 2,221.88 | 776.88 | 1,155.81 | 48.78 |
| 20 | 1,075.90 | 376.19 | 520.96 | 38.48 |

TABLE 12-continued

Effect of elderberry fruit extract (anthocyanins) on soluble ellagic acid content in muscadine pomace extract.

| | Soluble ellagic acid content (µg/ml) | | | |
|---|---|---|---|---|
| % solids | Muscadine pomace extract (measured) | Muscadine pomace extract/elderberry fruit extract mixture (expected) | Muscadine pomace extract/elderberry fruit extract mixture (measured) | % increase over predicted |
| 10 | 411.25 | 143.79 | 238.34 | 65.76 |
| 2 | 74.81 | 26.16 | 39.14 | 49.62 |

These results clearly illustrate that the muscadine pomace extract/elderberry fruit extract contained considerably greater amounts (40-65% more) of soluble ellagic acid than that predicted by the contribution of muscadine pomace extract. Although the muscadine pomace extract was prepared from a mixture of bronze and purple pomace extracts and thus contained anthocyanins from the purple pomace (thus promoting ellagic acid solubility), the addition of anthocyanins from a source other than muscadine (elderberry fruit extract) appeared to augment ellagic acid solubility even further.

Confirmation of this idea was sought by measuring the absolute value of total ellagic acid in the muscadine pomace extract to learn what portion of the total ellagic acid content was soluble under the conditions described above. To determine the absolute value of total ellagic acid contained within the samples, each dried powder (samples 1 and 2) was dissolved in DMSO and their ellagic acid contents were assessed as described above (total area of ellagic acid was measured by reverse phase HPLC with UV-VIS detection at 254 nm in tandem with a Ion-Trap mass detector, using extracted ion chromatogram (EIC) at $[M-H]^-=301$ amu). The following tables (13 and 14) show that the percentage of total ellagic acid that becomes soluble was enhanced by both endogenous muscadine pomace anthocyanins and by the addition of exogenous anthocyanins from elderberry fruit extract.

TABLE 13

Effect of muscadine pomace anthocyanins on the solubility of total ellagic acid in muscadine pomace extract.

| | Ellagic acid content (µg/ml) | | |
|---|---|---|---|
| % solids | Muscadine pomace extract (total content) | Muscadine pomace extract (soluble content) | % of total ellagic acid that is soluble |
| 40 | 4,360.00 | 2,221.88 | 50.96 |
| 20 | 2,180.00 | 1,075.90 | 49.35 |
| 10 | 1,090.00 | 411.25 | 37.73 |
| 2 | 218.00 | 74.81 | 34.32 |

Table 13 shows that the endogenous anthocyanins in the muscadine pomace extract (from the purple pomace) enhanced the percentage of total ellagic acid that becomes solubilized. The increasing levels of solids content are attended by increasing content of endogenous anthocyanins and thus, the percentage of soluble ellagic acid rose from 34% to 50% of the total ellagic acid content contained within the muscadine pomace extract. Nevertheless, a maximum of only 50% of the total ellagic acid content of the muscadine pomace extract was solubilized by the endogenous anthocyanin content from the purple pomace.

TABLE 14

Effect of elderberry fruit extract (anthocyanins) on the solubility of total ellagic acid in muscadine pomace extract.

| | Ellagic acid content (µg/ml) | | |
|---|---|---|---|
| % solids | Muscadine pomace extract/elderberry fruit extract mixture (total content) | Muscadine pomace extract/elderberry fruit extract mixture (soluble content) | % of total ellagic acid that is soluble |
| 40 | 1,524.47 | 1,155.81 | 75.82 |
| 20 | 762.24 | 520.96 | 68.35 |
| 10 | 381.12 | 238.34 | 62.54 |
| 2 | 76.22 | 39.14 | 51.35 |

Table 14 shows that the inclusion of additional and exogenous anthocyanins from elderberry fruit extract greatly enhanced the solubility of the ellagic acid contained within the muscadine pomace extract. As the levels of solids were increased, the content of total anthocyanins (endogenous and exogenous) also increased and the percentage of soluble ellagic acid rose from 51% to 75% of the total ellagic acid content of the muscadine pomace extract. Moreover, the addition of exogenous anthocyanins from elderberry fruit extract enhanced the solubility of ellagic acid at all levels of solids content when compared to the muscadine pomace extract alone. Indeed, at the 40% solids level, the addition of exogenous anthocyanins from elderberry extract enabled the solubilization of 75% of the total ellagic acid content whereas the endogenous anthocyanins from the purple pomace solubilized only 50% of the total ellagic acid content. In conclusion, although the anthocyanins found in purple muscadine pomace enhance ellagic acid solubility of the muscadine pomace extract, additional anthocyanins from a source other than muscadine provide further surprising increases in ellagic acid solubility.

Example 7

Sample Formulations

An embodiment of the disclosed composition that has synergistic anti-oxidant activities contains a mixture of muscadine pomace extract and an additional source of polyphenols such as elderberry fruit extract (having a polyphenol content of at least 5.7%), in combination with an additional source of resveratrol other than muscadine or elderberry fruit extract. The source of additional resveratrol can for example be Japanese Knotweed root extract (at least 98% resveratrol). Suitable carriers and/or food flavorings and colorings can be added to the composition. For example, the carriers and/or food flavorings and colorings can include one or more or all of glycerin, colloidal silicon dioxide, natural flavors, purple carrot extract, sorbitol syrup and glycerin.

The muscadine pomace extract can be either a bronze muscadine pomace extract or a purple muscadine pomace extract, or a mixture of bronze and purple muscadine pomace extract, for example in a ratio of 0.1 to 10, for example 0.3 to 3.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An antioxidant composition, comprising:
   (a) a muscadine (*Vitis rotundifolia*) pomace solvent extract;
   (b) resveratrol from a source other than muscadine, wherein a ratio of muscadine pomace extract polyphenols to trans-resveratrol is in the range of 0.1/1 to 10/1 (weight to weight)
   (c) wherein the composition has a polyphenol content of at least 4%, and the polyphenol content includes anthocyanin from other than muscadine pomace,
   (d) wherein the muscadine pomace solvent extract comprises a mixture of bronze and purple muscadine pomace solvent extract in a ratio that ranges from 0.1 to 10 (weight to weight), and the muscadine pomace solvent extract is both filtered and fermented.

2. The composition of claim 1, wherein the polyphenol content of the composition is at least 10%.

3. The composition of claim 1, wherein the polyphenol content of the composition is 10-35%.

4. The composition of claim 1, wherein the muscadine pomace solvent extract is a concentrated muscadine pomace solvent extract.

5. The composition of claim 4, wherein the muscadine pomace solvent extract is a muscadine pomace solvent extract concentrated to a solids content of at least 40%.

6. The composition of claim 1, wherein the ratio of non-stilbene polyphenols to trans-resveratrol is at least 0.75 to 1, or the ratio of muscadine pomace solvent extract to resveratrol is in the range of 0.2/1 to 50/1.

7. The composition of claim 6, wherein the ratio of muscadine pomace extract to resveratrol is in the range of 5/1 to 50/1.

8. The composition of claim 7, wherein the ratio of muscadine pomace extract to resveratrol is in the range of 18 to 1.

9. The composition of claim 1, wherein the resveratrol from a source other than muscadine is from Japanese knotweed, melinjo (*Gnetum gnemon*), red wine, peanut shells or grapevines.

10. The composition of claim 1, wherein the anthocyanin from other than muscadine pomace is from elderberry, black currant, blueberry, black raspberry, red raspberry, blackberry, bilberry, cloudberry, chokeberry, gooseberry, grape or purple carrot, or a combination of two or more of elderberry, black currant, blueberry, black raspberry, red raspberry, blackberry, bilberry, cloudberry, chokeberry, gooseberry, grape or purple carrot.

11. The composition of claim 10, wherein the anthocyanin from other than muscadine pomace comprises anthocyanin from elderberry fruit or an extract thereof.

12. The composition of claim 11, wherein the anthocyanin from elderberry fruit comprises elderberry fruit extract.

13. The composition of claim 10, wherein anthocyanin from other than muscadine pomace is an extract of elderberry, black currant, blueberry, black raspberry, red raspberry, blackberry, bilberry, cloudberry, chokeberry, gooseberry, grape or purple carrot, or a combination of extracts of any one or more of elderberry, black currant, blueberry, black raspberry, red raspberry, blackberry, bilberry, cloudberry, chokeberry, gooseberry, grape or purple carrot.

14. The composition of claim 1, further comprising one or more of carriers, food flavorings, and colorings.

15. The composition of claim 1, wherein the muscadine solvent pomace extract is a water extract of muscadine pomace.

16. The composition of claim 1, wherein the polyphenol content from the anthocyanin is present in a ratio of 1:3 to 2:1 with polyphenols from the muscadine pomace solvent extract.

17. A method of inhibiting oxidation in a subject, by administering an antioxidative effective amount of the composition of claim 1.

18. The method of claim 17, wherein the method is a method of increasing $ORAC_{lipophilic}$ in a subject to whom the composition is administered.

19. The method of claim 17, wherein the composition further comprises polyphenols from a source other than muscadine pomace, and the effective amount of the composition increases one or more of mitochondrial oxygen consumption, mitochondrial biogenesis, lipophilic ORAC, or expression of mitochondrial biogenesis or antioxidant genes.

20. The method of claim 19, wherein the mitochondrial biogenesis genes comprise one or more of NRF1, SIRT3, COX, and the antioxidant genes comprise one or more of NRF2, NQO-1, and GST-P1.

21. A method of increasing antioxidant activity in lipophilic tissue, comprising selecting a subject in need of an increase in antioxidant activity and administering to the subject an amount of the composition of claim 1 effective to increase lipophilic antioxidant activity in the subject.

* * * * *